US006258776B1

United States Patent
Hemmings et al.

(10) Patent No.: US 6,258,776 B1
(45) Date of Patent: Jul. 10, 2001

(54) CALCIUM-REGULATED KINASE

(75) Inventors: Brian Arthur Hemmings, Bettingen; Thomas Anders Millward, Basel, both of (CH)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 09/133,062

(22) Filed: Aug. 12, 1998

(30) Foreign Application Priority Data

Aug. 12, 1997 (GB) .................................................. 9717089
Aug. 19, 1997 (GB) .................................................. 9717499

(51) Int. Cl.$^7$ .......................... A61K 38/10; A61K 38/16; C07K 14/00; C12Q 1/48; G01N 33/68
(52) U.S. Cl. .................................. 514/2; 435/15; 436/86; 514/12; 514/13; 514/14; 514/15; 530/300; 530/324; 530/328
(58) Field of Search ........................ 435/15, 194; 436/86; 514/2, 12, 13, 14, 15, 44; 530/300, 324, 328, 350

(56) References Cited

U.S. PATENT DOCUMENTS

| | | | |
|---|---|---|---|
| 4,434,160 | * 2/1984 | Jeretin et al. ........................... | 514/23 |
| 5,698,518 | * 12/1997 | Carson et al. ........................... | 514/12 |
| 5,837,684 | * 11/1998 | Orning et al. ........................... | 514/15 |
| 5,981,205 | * 11/1999 | Hemmings et al. .................... | 435/15 |
| 5,990,080 | * 11/1999 | Haglid ..................................... | 514/2 |

FOREIGN PATENT DOCUMENTS

| | | |
|---|---|---|
| 96/02643 | * 2/1996 | (WO) . |
| WO 96/19579 | 6/1996 | (WO) . |
| 96/30402 | * 10/1996 | (WO) . |

OTHER PUBLICATIONS

Leighton et al. Comparison of the specificites of p 70 Sbkinase . . . FEBS Letters. vol. 375, pp. 289–293, 1995.*
Baudier et al., Biochemistry, vol. 26, pp. 2886–2893 (1987).
Baudier et al., Biochemistry, vol. 34, pp. 7834–7846 (1995).
Baudier, FEBS Letters, vol. 147, No. 2, pp. 165–167 (1989).
Brook et al., Cell. vol. 68, pp. 799–808 (1992).
Brostrom et al., Annu. Rev. Physiol, vol. 52. pp. 577–590, (1990).
Cocchia et al., Nature, vol. 294, pp. 85–87 (1981).
Cochran et al., Melanoma Research, vol. 3, pp. 325–330 (1993).
Fan, Brain Research, vol. 237, pp. 498–503 (1982).
Favre et al., The Journal of Biological Chemistry, vol. 272, No. 21, pp. 13856–13863 (1997).
Goldberg et al., Cell, vol. 84, pp. 875–887, (1996).
Hanks et al., The Protein Kinase Facts Book, vol. 1, "2 The Eukaryotic Protein Kinase Superfamily", pp. 7–47 (1995), London Academic Press Harcourt Brace & Company, Publishers.
Heierhorst et al., Nature, vol. 380, pp. 636–639 (1996).
Heizmann et al., Trends in Biochem. Sci., vol. 16, pp. 98–103 (1991).
Hidaka et al., Methods In Enzymology, vol. 102, No. 17, pp. 185–194 (1983).
Hidaka et al., Proc. Natl. Acad. Sci, USA, vol. 78, No. 7, pp. 4354–4357 (1981).
Hyden et al., Proc. Natl. Acad. Sci., US, vol. 55, pp. 354–358 (1966).
Ike, Nucleic Acids Research, vol. 11, No. 2, pp. 477–489 (1983).
Ilg et al., Int. J. Cancer, vol. 68, pp. 325–332, (1996).
Isobe et al., Biochemistry International, vol. 6, No. 3, pp. 419–426 (1983).
Ivanenkov et al., The Journal of Biological Chemistry, vol. 270, No. 24, pp. 14651–14658 (1995).
James et al., Trends in Biochem. Sci., vol. 20, pp. 38–42, (1995).
Johnston et al., Mol. Cell Biol., vol. 10, No. 4, pp. 1358–1366, (1990).
Justice et al., Genes & Development, vol. 9, pp. 534–546 (1995).
Kao et al., J. Cell Biol. vol. 111, 183–196, (1990).
Kato et al., J. of Neurochemistry, vol. 46, No. 5, pp. 1555–1560 (1986).
Kemp et al., Structural Aspects, pseudosubstrate and substrate interations Protein Kinases, J. R. Woodgett ed. IRL Press, pp. 30–67 (1994).
Koff et al., Science, vol. 257, pp. 1689–1694 (1992).
Kretsinger et al., The EF–Hand, Homologs and analogs in Novel Calcium Binding Proteins; Fundamentals and Clinical Implications, pp. 17–37 (1991), Springer–Verlag, Berlin, (Heinzman, C.W., Ed.).
Lam et al., Proc. Natl. Acad. Sci., USA, vol. 91, pp. 6569–6573 (1994).
Leung et al., J. Biol. Chem, vol. 270, No. 49, pp. 29051–29054 (1995).
Marks et al., Experimental Cell Research, vol. 187, pp. 59–64 (1990).
Mattias et al., Nucleic Acids Research, vol. 17, No. 15, p. 6418 (1989).
Millward et al., Proc. Natl. Acad. Sci., USA, Biochemistry, vol. 92, pp. 5022–5026 (1995).
Millward. PhD Thesis, University of Basel (1997).
O'Neil et al., Trends Biochem., Sci., vol. 15, pp. 59–64 (1990).
Pedrocchi et al., Biochemistry, vol. 33, pp. 6732–6738 (1994).

(List continued on next page.)

*Primary Examiner*—Jeffrey E. Russel
(74) *Attorney, Agent, or Firm*—Hesna J. Pfeiffer

(57) ABSTRACT

The invention concerns a method of modulating the activity of a polypeptide comprising the activating domain of an Ndr family kinase, by influencing the binding of an EF hand-containing calcium binding.

5 Claims, No Drawings

OTHER PUBLICATIONS

Remppis et al., Biochemica et Biophysica Acta, vol. 1313, pp. 253–257 (1996).

Rhyner et al., Biochimica et Biophysica Acta, vol. 1313, pp. 179–186 (1996).

Schäfer et al., Trends Biochem Sci., vol. 21, pp. 134–140, (1996).

Seed et al., Proc. Natl. Acad. Sci., USA, vol. 84, pp. 3365–3369 (1987).

Selinfreund et al., The Journal of Cell Biology, vol. 111, pp. 2021–2028 (1990).

Smith et al., Biochemistry, vol. 35, pp. 8805–8814 (1996).

Stefansson et al., Nature, vol. 295, pp. 63–64 (1982).

Studier et al., Methods in Enzymol, vol. 185, pp. 60–89 (1990).

Taylor et al., J. Biol. Chem., vol. 264, No. 11, pp. 6207–6213 (1989).

Todoroki et al., The Journal of Biological Chemistry, vol. 266, No. 28, pp. 18668–18673 (1991).

Toyn et al., The EMBO Journal, vol. 13, No. 5, pp. 1103–1113 (1994).

Umekawa et al., Archives of Biochemistry and Biophysics, vol. 227, No. 1, pp. 147–153 (1983).

Werlen et al., J. Biol. Chem., vol. 268, No. 22, pp. 16596–16601 , (1993).

Xu et al., Development, vol. 121, pp. 1053–1063 (1995).

Yang et al., Developmental Brain Res., vol. 91, pp. 181–189, (1996).

Yarden et al., The EMBO Journal, vol. 11, No. 6, pp. 2159–2166 (1992).

Baudier, J. of Biol. Chem., vol. 261, No. 18, pp. 8192–8203 (1986).

Hanks et al., Methods in Enzymology, vol. 200, pp. 38–62 (1991).

Schaefer et al., Genomics, vol. 25, pp. 638–643 (1995).

* cited by examiner

CALCIUM-REGULATED KINASE

The present invention relates to kinase proteins of the nuclear Dbf2-related (Ndr) protein kinase family and to the activation thereof in response to calcium signalling.

Reversible protein phosphorylation is a major mechanism for the co-ordinated control of many fundamental cellular functions in eukaryotic organisms, including metabolism, growth, and differentiation. The phosphorylation status, and consequently the activity, of specific target proteins is regulated by the opposing actions of protein kinases and protein phosphatases. Generally, these enzymes are specific either for serine/threonine or for tyrosine phosphoacceptors, although some dual specificity kinases and phosphatases have also been described. The importance of phosphorylation cascades is reflected by the finding that many kinases, phosphatases, and the signal transduction pathways in which they participate have been highly conserved during the course of evolution. In recent years, interest has focused on the role of protein phosphorylation in the control of the cell cycle; a number of cellular proto-oncogenes encode members of the serine/threonine kinase family and it has become increasingly clear that certain serine/threonine kinases function as key components of the cell cycle regulatory network. Therefore, the complete delineation of these pathways is an important aim for the understanding of oncogenesis and tumour progression.

Ndr is a nuclear serine/threonine protein kinase that was recently cloned from human brain, *D. melanogaster* and *C. elegans* cDNA libraries (Millward, T. A., et aL, (1995) *Proc. Natl. Acad. Sci. USA* 92, 5022–5026). Although the high level of conservation of Ndr between these species implies an important role in cellular physiology, its function is currently unknown. Possible clues are, however, suggested by its phylogenetic relationship to several serine/threonine kinases from lower eukaryotes which have been identified in genetic screens as essential for normal cell growth and morphology. This emerging subfamily of protein kinases presently comprises, in addition to Ndr, Wts/lats (a tumour suppressor gene product from *D. melanogaster*), cot-1 (required for growth by hyphal elongation in N. crassa) and Dbf2/Dbf20 (budding yeast cell cycle-regulated kinases with a metaphase/anaphase function) (Justice, R. W., et al., (1995) *Genes Dev.* 9, 534–546; Xu, T., et al., (1995) *Development* 121, 1053–1063; Yarden, O., et al., (1992) *EMBO J,* 11, 2159–2166; and Toyn, J. H. and Johnston, L. H. (1994) *EMBO J.* 13,1103–1113). These kinases share 40–60% amino acid identity in their catalytic domains and show several conserved features outside of their catalytic domains. For example, a hallmark of this group of kinases is that each contains an "insert" in its catalytic domain, located between subdomains VII and VIII, which is not present in other protein kinases. Two mammalian kinases, ROKα (Leung, T., et al., (1995) *J. Biol. Chem.* 270, 29051–29054) and the myotonic dystrophy kinase DMK (Brook, J. D., et al., (1992) *Cell* 68, 799-808), are also related to this subfamily, although they do not contain the kinase domain insert. In the superfamily of serine/threonine protein kinases, this kinase subfamily falls within the second messenger-regulated ("AGC") group (Hanks, S. K. and Hunter, T. (1995) in *The protein kinase facts book: protein-serine kinases* (Hardie, G. and Hanks, S. K., eds) pp. 7–47, Academic Press Ltd., London). However, while genetic studies have been instrumental in defining the possible functions of these kinases, their regulation is only partially understood. ROKα is activated by interaction with the GTP-bound form of RhoA; however, binding to RhoA is mediated by a domain of ROKα not present in the other kinases (Leung et al., *Op. Cit.*), suggesting that these kinases are regulated by other mechanisms.

Binding of growth factors and peptide hormones to cell surface receptors leads to transient increases in the intracellular concentrations of several "second messengers." One such second messenger is $Ca^{2+}$, which elicits multiple cellular responses primarily by binding to a large family of EF hand-containing proteins (Hunziker, W. and Heizmann, C. W. (1991) *Trends Biochem. Sci.* 16, 98–103; James, P., et al., (1995) *Trends Biochem. Sci.* 20, 38–42). This family includes, among others, calmodulin (CaM) and S100 proteins. Binding of $Ca^{2+}$ to these proteins induces a conformational change in the polypeptide which exposes a hydrophobic surface capable of binding to secondary effector proteins. $Ca^{2+}$ fluxes play an important role in the regulation of cell motility, cell division, transcription, protein synthesis and apoptosis. This diversity of function may be possible because $Ca^{2+}$ binds to multiple classes of EF hand proteins, each of which can, in turn, regulate multiple downstream effectors.

WO96/19579 discloses that Ndr protein kinase is capable of binding to calmodulin, a major calcium-binding protein of the EF hand family. This suggested that calmodulin may play a role in the activation of Ndr. However, this determination was made without access to an efficient assay for Ndr activity, because none existed at the time; the substrates commonly used for other protein kinases, such as histone, myelin basic protein and casein, are not substrates for Ndr. Moreover, the site of calmodulin binding to Ndr was not disclosed.

SUMMARY OF THE INVENTION

Employing a novel and effective test for Ndr activity, it has now been determined that calmodulin is a weak, but not a major, in vitro activator of Ndr. Ndr is, however, regulated by $Ca^{2+}$concentration, and is activated by two calmodulin-related polypeptides, S100B and S100 in a calcium-dependent manner. Both S100B and S100 bind Ndr in the N-terminal region, exerting their activatory activity at this site. The binding site appears to coincide or overlap with the calmodulin binding site, suggesting that both calmodulin and the S100 proteins bind Ndr in a similar manner. Furthermore, it has now been shown that Ndr is negatively regulated by protein phosphatase 2A (PP2A), a phosphoserine/phosphothreonine phosphatase.

In a first aspect of the present invention, therefore, there is provided a method of modulating the activity of a polypeptide comprising the activating domain of an Ndr family kinase, by influencing the binding of an EF hand-containing calcium binding protein to the Ndr family kinase activating domain.

In a further aspect, the invention provides agents capable of influencing the binding of EF-hand containing polypeptides to the N-terminal binding domain of an Ndr family kinase. Preferably, the agents may be based on peptides derived from the binding domain.

Moreover, the invention provides a method for screening potential activators or repressors of Ndr family kinase activity, by (a) screening compounds for the ability to bind to the N-terminal binding domain of Ndr family kinase, or to modulate the binding of EF hand-containing polypeptides to this domain, and/or by (b) screening candidate compounds for the ability to modulate the activity of Ndr family kinase in vitro.

Ndr activity may be measured according to a further aspect of the invention, which provides a method for assessing Ndr activity comprising determining the ability of Ndr to phosphorylate a target peptide $B_1 B_2 B_3 \times B_4 B_5 \times S \ n \ x$, where at least two of $B_{1-5}$ are basic amino acids, the remainder of $B_{1-5}$ being any amino acid, x is any amino acid, n is any amino acid except proline and S is serine. Also provided are peptides suitable for use in this aspect of the invention, having the above general formula.

Moreover, the present invention provides a pharmaceutical composition comprising an EF-hand containing calcium binding protein, or a molecular mimic or regulator thereof, as well as the use of an EF-hand containing calcium binding protein, or a molecular mimic or regulator thereof in the manufacture of a composition for modulating the activity of a polypeptide comprising the activating domain of an Ndr family kinase.

DETAILED DESCRIPTION OF THE INVENTION

Ndr protein kinase is a member of a subgroup of protein kinases that includes D. melanogaster Wts/lats, N. crassa cot-1 and S. cerevisiae Dbf2/Dbf20. These kinases show 55%, 54% and 40% catalytic domain identity to Ndr, respectively, and also share significant homology outside of their catalytic domains. Wts/lats, cot-1 and Dbf2 were all isolated in genetic screens for mutations that affect cell cycle progression or cell morphology. Two mammalian kinases, ROKα and DMK, are also members of this subfamily. With the exception of ROKα, the mechanism of regulation of these kinases has hitherto been poorly defined.

The CaM/S100 binding domain of Ndr is well conserved in Wts/lats, cot-1 and Dbf2. It is referred to herein as the "CaM/Si 00 binding domain" or the "activating domain" of Ndr.

For all currently known protein kinases that are regulated by CaM, the mechanism of activation involves binding of CaM to an autoinhibitory region which is located carboxy terminally to the kinase catalytic domain. Binding of CaM then changes the conformation of this region and consequently causes release of the intrasteric inhibition. A similar mechanism applies for twitchin kinase regulation by S100A1. These kinases can be activated in vitro by deletion or proteolysis of the autoinhibitory domain. In contrast, the CaM/S100 binding domain of Ndr is amino terminal to the kinase domain, and is clearly not autoinhibitory. Therefore, Ndr is representative of a new class of calcium-regulated protein kinases that are subject to a novel mechanism of activation, and which includes Ndr, Wts/lats, cot-1, Dbf2, ROKα and DMK. These kinases are referred to herein as "Ndr family kinases".

Preferably, "Ndr family kinases" are those kinases which comprise a domain homologous to the CaM/S100 binding domain of Ndr. These kinases include Ndr, Wts/lats, cot-1 and Dbf2. In its most preferred embodiment, the present invention is concerned with Ndr protein kinase. Preferably, it is human Ndr kinase.

The activating or CaM/S100 binding domain of Ndr protein kinase is located at the N-terminus thereof. Preferably, this domain comprises amino acids 1 to 84 of Ndr. The domain may be used in its entirety, or, in a preferred aspect of the invention, the region thereof directly responsible for CaM/S100 binding and Ndr activation may be used in isolation from the remaining sequences comprised in this domain. Advantageously, the domain includes at least residues 72 to 84 of the entire Ndr domain. As defined herein, however, the "domain" includes those residues necessary for EF hand-containing protein activation of Ndr family kinases. Advantageously, the domain consists essentially of a peptide as described below.

The present invention provides peptides which encompass the S100/CaM binding domain of Ndr family kinases. Peptides according to the invention preferably encompass the active part of the binding domain, which itself spans amino acids 1 to 84 of the amino terminus of Ndr. Thus, peptides according to the invention may take the form of the whole of the amino terminus of Ndr, or the equivalent domain of another Ndr family kinase, or a truncated or modified form thereof. Preferred peptides are defined hereinbelow, under the heading "Modulation of Interactions at the Binding Site". Preferably, at least amino acids 72 to 84 are retained.

In a further embodiment, the invention provides fusion proteins which comprise a peptide according to the invention. Such fusion proteins comprise the active part of the S100/CaM binding domain of an Ndr family kinase, preferably located at the N-terminus of the fusion protein. Inclusion of a peptide according to the invention in the fusion protein may permit regulation thereof with an EF hand-containing calcium binding protein.

EF hand-containing calcium-binding proteins (CBP) are as defined in Hunziker and Heizmann, Op. Cit. and James et al., Op. Cit.). The family includes, amongst others, S100A2, S100A4, S100A6, S100A1, S100B and CaM. Preferably, the EF hand-containing proteins according to the invention are selected from the group consisting of S100A1, S100B and CaM. Most preferably, they are S100A1 or S100B. Although CaM and some other members of the EF hand-containing family have only a small modulating effect on Ndr activation, S100A1 and S100B have activating effects of 2-3 fold and 5–6 fold respectively, indicating that they are more potent Ndr activators.

The binding of EF hand-containing CBP to the activating or S100/CaM binding site of an Ndr family kinase may be influenced in a variety of ways in accordance with the present invention.

Modulation of EF hand-containing CBP levels

The modulating effect of CBP on Ndr family kinases may be directly influenced by raising or lowering the levels of the CBP in vivo or in vitro. This may be achieved, for example, by transfecting a cell with a vector encoding a CBP in order to raise the levels thereof in vivo. Suitable vectors and transfection protocols are known to those skilled in the art and are further described, by way of example, below.

Alternatively, CBP levels may be modulated in vivo by altering the expression levels of endogenous CBP genes, for example by employing agents which affect transcription and/or translation of CBPs. For example, antisense molecules may be designed according to techniques known in the art and directed to particular CBPs to block the translation, post-transcriptional processing and/or transcription thereof (for example, see Selinfreund, R. H., et al., (1990) J. Cell Biol. 111, 2021–2028). Genes encoding antisense molecules may be transfected into cells to express the molecules in situ. Moreover, ribozymes may be used to achieve a similar effect, by selectively cleaving or blocking CBP mRNA in vivo or in vitro and thus lowering the levels of CBP.

The foregoing techniques lend themselves to methods of gene therapy wherein nucleic acids containing CBP-encoding sequences, or sequences containing ribozymes or antisense molecules directed against CBP-encoding nucleic acids, are transfected into an organism such that the CBP, antisense molecule or r,;bozyme is produced in situ. Various functions have been ascribed to CBPs including roles in the regulation of transcription, differentiation, cell cycle progression and cell morphology (Schäfer, B. W. and Heizmann, C. W. (1996) *Trends Biochem. Sci.* 21, 134–140). Studies using antisense oligonucleotides to inhibit S100B expression in cultured cells showed that depletion of S100B causes a reduced proliferative rate, and a more flattened cell morphology. In vitro S100B and S100A1 can influence microtubule dynamics. Evidence implicating S100B in the regulation of cell proliferation is provided by the findings that S100B mRNA levels are subject to cell cycle regulation, and that S100B is highly overexpressed (~100-fold) in the majority of melanoma cell lines relative to untransformed melanocytes (Cocchia, D., et al., (1981) *Nature* 294, 85–87; Marks, M., et al., (1990) *Exp. Cell. Res.* 187, 59–64). In fact, anti-S100B antibodies are widely used for diagnosis of melanoma (Cochran, A. J., et al., (1993) *Melanoma Res.* 3, 325–330). Based on these results as well as on the findings which have led to the present invention showing that Ndr is activated by $Ca^{2+}$/S100B and that Ndr is hyperactivated in S100B overexpressing melanoma cells, Ndr represents a potential target for anti-melanoma drug therapy. Accordingly, there are provided antagonists of the Ndr-S100B interaction which are e.g. non-peptidic mimetics of the peptide KRLRRSAHARKETEFLRLKRTRLGL (SEQ ID No.32) that has been shown to effectively inhibit binding of S100B to Ndr. Furthermore, inhibitors are provided that bind to the catalytic domain of Ndr.

Gene therapy approaches are particularly applicable for the treatment of diseases or disorders involving Ndr regulation by CBPs, for example those conditions which involve deficiencies in transcription, differentiation, cell cycle progression and cell morphology as set forth above. In particular, gene therapy approaches may be used for the treatment of tumours, preferably melanomas.

In a further aspect, CBP levels may be modulated in vitro simply by adding more or less CBP to an in vitro reaction, as desired. This approach is applicable in screening systems, assays for kinase activity and other in vitro procedures. CBP levels may be modulated where the CBP is bound to a solid phase, such as an agarose column, by varying the amount of CBP complexed per unit of solid phase material.

Modulation of Ndr Family Kinase Levels

The techniques described above for the modulation of CBP levels may be employed for the modulation of the levels of the kinase itself. In either eventuality, the activity of the Ndr family kinase is modulated by affecting the levels of active kinase.

Modulation of Interactions at the Binding Site

In an advantageous aspect, the invention provides for the modulation of the interaction between CBPs and Ndr family kinases at the level of the binding site. This may be performed in a number of ways, including for example (a) administering a molecular mimic of the binding site of the CBP, thus competing for binding sites on the Ndr family kinase and reducing effective CBP-Ndr interaction; (b) administering a molecular mimic of the binding site of the Ndr family kinase, thus competing for binding sites on the CBP and reducing effective CBP-Ndr interaction; (c) administering an agent capable of causing an alteration in the binding site of the CBP and/or the Ndr family kinase, such as a conformational change, thereby affecting CBP-Ndr binding; (d) administering a modified Ndr family kinase or a modified CBP wherein the binding site has been modified, for example by selective mutagenesis, to provide for improved, reduced or altered specificity of binding; (e) administering a substance, other than a molecular mimic, which is capable of binding to the CBP and/or Ndr family kinase binding site, thus impeding CBP-Ndr interaction.

Molecular mimics may, for example, be peptides derived from the CBP/Ndr binding site of a CBP or an Ndr family kinase. Such peptides, for example, may selected from the domain comprising amino acids 1–84 of Ndr, or the homologous domain of another Ndr family kinase. Alternatively, the peptides may be selected from the corresponding binding domain on a CBP.

If appropriate, the entire 1–84 amino acid domain may be used. However, advantageously a smaller peptide is selected. Preferable, such a peptide may comprise 5 to 80, more preferably 10 to 60, 20 to 50, 20 to 40 or 25 to 30 continuous amino acids from the Ndr family kinase binding domain. Most preferably, the peptide comprises about 25 amino acids.

In a most preferred embodiment of this aspect of the invention, the peptide is 25 amino acids in length and has the sequence KRLRRSAHARKETEFLRLKRTRLGL (SEQ. ID. No. 32).

Moreover, the peptide may be comprised of non-continuous amino acids from the Ndr family kinase domain; in other words, deletions, alterations or insertions may be performed in the domain to alter the properties of the peptide. For example, the peptide may be altered such that its binding constant for a particular CBP is greater than, or lesser than, that of the wild type Ndr family kinase, thus altering the modulatory effect of the peptide.

Peptides comprising deletions and insertions are variants of the Ndr family kinase binding domain. The variant provided by the present invention includes splice variants encoded by mRNA generated by alternative splicing of a primary transcript, amino acid mutants, glycosylation variants and other covalent derivatives of the Ndr activating domain which retain the physiological and/or physical properties of Ndr activating domain. Exemplary derivatives include molecules wherein the domain of the invention is covalently modified by substitution, chemical, enzymatic, or other appropriate means with a moiety other than a naturally occurring amino acid. Such a moiety may be a detectable moiety such as an enzyme or a radioisotope. Further included are naturally occurring variants of Ndr activating domain found within a particular species, preferably a mammal. Such a variant may be encoded by a related gene of the same gene family, by an allelic variant of a particular gene, or represent an alternative splicing variant of an Ndr family kinase gene.

Variants which retain common structural features can be fragments of the Ndr activating domain. Fragments of the Ndr activating domain comprise smaller polypeptides derived from therefrom. Preferably, smaller polypeptides derived from the Ndr activating domain according to the invention define a single feature which is characteristic of the Ndr activating domain. Fragments may in theory be almost any size, as long as they retain the activity of the Ndr activating domain described herein.

Derivatives of the Ndr activating domain also comprise mutants thereof, which may contain amino acid deletions, additions or substitutions, subject to the requirement to maintain the activity of the Ndr activating domain described herein. Thus, conservative amino acid substitutions may be made substantially without altering the nature of the Ndr activating domain, as may truncations from the 5' or 3' ends. Deletions and substitutions may moreover be made to the fragments of the Ndr activating domain comprised by the invention. Ndr activating domain mutants may be produced from a DNA encoding the Ndr activating domain which has been subjected to in vitro mutagenesis resulting e.g. in an addition, exchange and/or deletion of one or more amino acids. For example, substitutional, deletional or insertional variants of the Ndr activating domain can be prepared by recombinant methods and screened for immunocrossreactivity with the native forms of the Ndr activating domain.

The fragments, mutants and other derivative of the Ndr activating domain preferably retain substantial homology with the Ndr activating domain. As used herein, "homology" means that the two entities share sufficient characteristics for the skilled person to determine that they are similar in origin and function. Preferably, homology is used to refer to sequence identity. Thus, the derivatives of the Ndr activating domain preferably retain substantial sequence identity with activating domain of Ndr.

"Substantial homology", where homology indicates sequence identity, means more than 40% sequence identity, preferably more than 45% sequence identity and most preferably a sequence identity of 50% or more.

The invention therefore provides a pharmaceutical composition comprising a peptide which is a molecular mimic of the CBP and/or Ndr family kinase binding site. The composition may be formulated according to procedures well known to those skilled in the art, which are discussed for exemplification below.

In another embodiment, the invention provides a peptide as defined above as a lead compound for the development of alternative compounds, such as low molecular weight compounds, which possess the same activity. This may be achieved in a number of ways; for example, the structure of the peptide may be modelled, for example by using computer assisted modelling techniques, and low molecular weight compounds designed such that they fit the binding site. In a particularly advantageous embodiment of the invention, the crystal structure of the peptide and/or a peptide/binding partner complex may be resolved. This will provide accurate information concerning the actual interaction between the peptide and Ndr/CPB, allowing the precise design of a molecule designed to mimic this interaction at the precise binding site.

Alternatively, the peptide may be used in biological or biochemical approaches to drug discovery to identify a substance which is, for example, able to displace it from its binding site on a CBP or Ndr family kinase. For example, compounds, preferably low molecular weight compounds, may be screened in a method comprising the steps of:

(a) forming a complex between a peptide according to the invention and its relevant binding partner;
(b) incubating the complex with the compound to be screened, and monitoring for dissociation of the peptide/binding partner complex; and
(c) selecting those compounds which either favour or impede dissociation of the complex, compared to a control background.

In preferred embodiments, DNA encoding a peptide is ligated into a vector, and introduced into suitable host cells to produce transformed cell lines that express the peptide. The resulting cell lines can then be produced for reproducible qualitative and/or quantitative analysis of the effect(s) of potential drugs affecting Ndr or CPB function. Thus peptide expressing cells may be employed for the identification of compounds, particularly small molecular weight compounds, which modulate the function of CBP or Ndr family kinases. Host cells expressing a peptide according to the invention are useful for drug screening and it is a further object of the present invention to provide a method for identifying compounds which modulate the activity of a CBP or Ndr family kinase, said method comprising exposing cells containing heterologous DNA encoding a peptide according to the invention, wherein said cells produce a functional CBP and an Ndr family kinase which is a natural target therefor, to at least one compound or mixture of compounds or signal whose ability to modulate the activity of the CBP/Ndr interaction is sought to be determined, and thereafter monitoring said cells for changes caused by said modulation. Such an assay enables the identification of modulators, such as agonists, antagonists and allosteric modulators, of Ndr family kinases or CBPs. As used herein, a compound or signal that modulates the activity of an NDR family kinase or CBP refers to a compound that alters the activity of the Ndr family kinase in such a way that the activity is different in the presence of the compound or signal as compared to the absence of said compound or signal.

Cell-based screening assays can be designed by constructing cell lines in which the expression of a reporter protein, i.e. an easily assayable protein, such as p galactosidase, chloramphenicol acetyltransferase (CAT) or luciferase, is dependent on the activity of an Ndr family kinase. Such an assay exploits, for example, the known ability of Ndr to modulate transcription, and enables the detection of compounds that directly modulate the interaction in question, such as compounds that antagonise Ndr/CBP binding. Alternatively, the test can be set up to assess the effect of the compound on Ndr activity by monitoring the biological response of the cells to Ndr. As set forth above, Ndr is known to be involved in the regulation of differentiation, cell cycle progression and cell morphology, all of which can be detected on the basis of cell appearance and/or cell survival capability.

The present invention also provides a method to exogenously affect CBP/Ndr interactions occurring in cells. Ndr family kinase and CBP producing host cells, e.g. mammalian cells, can be contacted with a test compound, and the modulating effect(s) thereof can then be evaluated by comparing an Ndr family kinase mediated response in the presence and absence of test compound.

Kinase response may be measured by assessing kinase activity. In a further aspect of the present invention, there is provided a test for Ndr family kinase activity comprising determining the ability of Ndr to phosphorylate a target peptide B. $B_2$ $B_3$ x $B_4$ $B_5$ x S n x SEQ ID NO:33, where at least two of $B_{1-5}$ are basic amino acids, the remainder of B. r being any amino acid, x is any amino acid, n is any amino acid except proline and S is serine. The serine residue in the peptide is the phosphoacceptor serine.

Preferably, $B_1$–$B_3$ are K or R. Most preferably, $B_1$–$B_3$ are K-K-R. At least one of $B_4$–$B_5$ is preferably R; advantageously, they are both R. Of the remaining amino acids, n is preferably an amino acid such as V, whilst x may be any amino acid, including such amino acids as N, L or A.

Accordingly, a preferred general formula for the peptide of the invention is K K R x R R x S n x, SEQ ID NO:34 wherein x and n are as defined above. Most preferably, the peptide has the formula K K R N R R L S VA (SEQ. ID. No. 1).

The kinase activity of the Ndr family kinase is measured by assessing the phosphorylation of the target peptide on exposure to the kinase. This will be apparent as serine phosphorylation. Advantageously, this may be measured by quantitating the incorporation of a labelled phosphate group into the peptide. For example, the phosphorylation reaction may be carried out in the presence of [$\gamma$-$_{32}$P] ATP. Alternatively, an enzyme-linked or chromogenic label may be used.

The kinase enzyme itself and the peptide are preferably separable before activity determination, in order to separate the peptide phosphorylation events from, for example, kinase autophosphorylation. Thus, in a preferred embodiment, the kinase and/or the peptide may be immobilised on a solid phase to assist separation. Preferably, the kinase is bound to a solid phase.

The invention also provides a pharmaceutical composition comprising an EF-hand containing calcium binding protein, or a molecular mimic or regulator thereof. The regulator may, for example, be a mimic of the CBP binding site found on an Ndr family kinase. A pharmaceutical composition according to the invention is a composition of matter comprising the EF-hand containing calcium binding protein, or a molecular mimic or regulator thereof as active ingredients. The active ingredients of a pharmaceutical composition according to the invention are contemplated to exhibit excellent therapeutic activity, when administered in amount which depends on the particular case. Dosage regima may be adjusted to provide the optimum therapeutic response. For example, several divided doses may be administered daily or the dose may be proportionally reduced as indicated by the exigencies of the therapeutic situation.

The active compound may be administered in a convenient manner such as by the oral, intravenous (where water soluble), intramuscular, subcutaneous, intranasal, intradermal or suppository routes or implanting (e.g. using slow release molecules). Depending on the route of administration, the active ingredient may be required to be coated in a material to protect said ingredients from the action of enzymes, acids and other natural conditions which may inactivate said ingredient.

In order to administer the combination by other than parenteral administration, it will be coated by, or administered with, a material to prevent its inactivation. For example, the combination may be administered in an adjuvant, co-administered with enzyme inhibitors or in liposomes. Adjuvant is used in its broadest sense and includes any immune stimulating compound such as interferon. Adjuvants contemplated herein include resorcinols, non-ionic surfactants such as polyoxyethylene oleyl ether and n-hexadecyl polyethylene ether. Enzyme inhibitors include pancreatic trypsin.

Liposomes include water-in-oil-in-water CGF emulsions as well as conventional liposomes.

The active compound may also be administered parenterally or intraperitoneally. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions (where water soluble) or dispersions and sterile powders for the extemporaneous preparation of sterile injectable solutions or dispersion. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene gloycol, and the like), suitable mixtures thereof, and vegetable oils. The proper fluidity can be maintained, for example, by the use of a coating such as lecithin, by the maintenance of the required particle size in the case of dispersion and by the use of superfactants.

The prevention of the action of microorganisms can be brought about by various antibacterial and antifungal agents, for example, parabens, chlorobutanol, phenol, sorbic acid, thirmerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin.

Sterile injectable solutions are prepared by incorporating the active compound in the required amount in the appropriate solvent with various of the other ingredients enumerated above, as required, followed by filtered sterilisation. Generally, dispersions are prepared by incorporating the sterilised active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

When the combination of polypeptides is suitably protected as described above, it may be orally administered, for example, with an inert diluent or with an assimilable edible carrier, or it may be enclosed in hard or soft shell gelatin capsules, or it may be compressed into tablets, or it may be incorporated directly with the food of the diet. For oral therapeutic administration, the active compound may be incorporated with excipients and used in the form of ingestible tablets, buccal tablets, troches, capsules, elixirs, suspensions, syrups, wafers, and the like. The amount of active compound in such therapeutically useful compositions in such that a suitable dosage will be obtained.

The tablets, troches, pills, capsules and the like may also contain the following: a binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavouring agent such as peppermint, oil of wintergreen, or cherry flavouring. When the dosage unit form is a capsule, it may contain, in addition to materials of the above type, a liquid carrier.

Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavouring such as cherry or orange flavour. Of course, any material used in preparing any dosage unit form should be pharmaceutically pure and substantially non-toxic in the amounts employed. In addition, the active compound may be incorporated into sustained-release preparations and formulations.

As used herein "pharmaceutically acceptable carrier and/or diluent" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, use thereof in the therapeutic compositions is contemplated. Supplementary active ingredients can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutical carrier. The specification for the novel dosage unit forms of the invention are dictated by and directly dependent on (a) the unique characteristics of the active material and the particular therapeutic effect to be achieved, and (b) the limitations inherent in the art of compounding such as active material for the treatment of disease in living subjects having a diseased condition in which bodily health is impaired.

The principal active ingredients are compounded for convenient and effective administration in effective amounts with a suitable pharmaceutically acceptable carrier in dosage unit form. In the case of compositions containing supplementary active ingredients, the dosages are determined by reference to the usual dose and manner of administration of the said ingredients.

In a further aspect there is provided the combination of the invention as hereinbefore defined for use in the treatment of disease. Consequently there is provided the use of an EF-hand containing calcium binding protein, or a molecular mimic or regulator thereof, in the manufacture of a composition for modulating the activity of a polypeptide comprising the activating domain of an Ndr family kinase.

General Methodology

Crystallisation involves the preparation of a crystallisation buffer, for example by mixing a solution of the peptide or peptide complex with a "reservoir buffer", preferably in a 1:1 ratio, with a lower concentration of the precipitating agent necessary for crystal formation. For crystal formation, the concentration of the precipitating agent is increased, for example by addition of precipitating agent, for example by titration, or by allowing the concentration of precipitating agent to balance by diffusion between the crystallisation buffer and a reservoir buffer. Under suitable conditions such diffusion of precipitating agent occurs along the gradient of precipitating agent, for example from the reservoir buffer having a higher concentration of precipitating agent into the crystallisation buffer having a lower concentration of precipitating agent. Diffusion may be achieved for example by vapour diffusion techniques allowing diffusion in the common gas phase. Known techniques are, for example, vapour diffusion methods, such as the "hanging drop" or the "sitting drop" method. In the vapour diffusion method a drop of crystallisation buffer containing the protein is hanging above or sitting beside a much larger pool of reservoir buffer. Alternatively, the balancing of the precipitating agent can be achieved through a semipermeable membrane that separates the crystallisation buffer from the reservoir buffer and prevents dilution of the protein into the reservoir buffer.

In the crystallisation buffer the peptide or peptide/binding partner complex preferably has a concentration of up to 30 mg/ml, preferably from about 2 mg/ml to about 4 mg/ml.

Formation of crystals can be achieved under various conditions which are essentially determined by the following parameters: pH, presence of salts and additives, precipitating agent, protein concentration and temperature. The pH may range from about 4.0 to 9.0. The concentration and type of buffer is rather unimportant, and therefore variable, e.g. in dependence with the desired pH. Suitable buffer systems include phosphate, acetate, citrate, Tris, MES and HEPES buffers. Useful salts and additives include e.g. chlorides, sulphates and further salts specified in Example 1. The buffer contains a precipitating agent selected from the group consisting of a water miscible organic solvent, preferably polyethylene glycol having a molecular weight of between 100 and 20000, preferentially between 4000 and 10000, or a suitable salt, such as a sulphates, particularly ammonium sulphate, a chloride, a citrate or a tartarate.

A crystal of a peptide or peptide/binding partner complex according to the invention may be chemically modified, e.g. by heavy atom derivatization. Briefly, such derivatization is achievable by soaking a crystal in a solution containing heavy metal atom salts, or a organometallic compounds, e.g. lead chloride, gold thiomalate, thimerosal or uranyl acetate, which is capable of diffusing through the crystal and binding to the surface of the protein. The location(s) of the bound heavy metal atom(s) can be determined by X-ray diffraction analysis of the soaked crystal, which information may be used e.g. to construct a three-dimensional model of the peptide.

A three-dimensional model is obtainable, for example, from a heavy atom derivative of a crystal and/or from all or part of the structural data provided by the crystallisation. Preferably building of such model involves homology modelling and/or molecular replacement.

The preliminary homology model can be created by a combination of sequence alignment with any of the Ndr family protease the sequence of which is known, secondary structure prediction and screening of structural libraries. For example, the sequences of Ndr and Dbf2 can be aligned using a suitable software program.

Computational software may also be used to predict the secondary structure of the peptide or peptide complex. The peptide sequence may be incorporated into the Ndr structure. Structural incoherences, e.g. structural fragments around insertions/deletions can be modelled by screening a structural library for peptides of the desired length and with a suitable conformation. For prediction of the side chain conformation, a side chain rotamer library may be employed.

The final homology model is used to solve the crystal structure of the peptide by molecular replacement using suitable computer software. The homology model is positioned according to the results of molecular replacement, and subjected to further refinement comprising molecular dynamics calculations and modelling of the inhibitor used for crystallisation into the electron density.

Recombinant DNA Technology.

In general, recombinant DNA methodology is as described in standard laboratory texts, including Sambrook et al., Molecular Cloning; a Laboratory Manual, Cold Spring Harbor, 1989. More specific teachings may also be referred to, as required, including the following. if required, nucleic acids encoding Ndr family kinases and/or CBPs may be cloned from tissues according to established procedures using probes derived from Ndr, S100A1 or any of the published sequences of related polypeptides. In particular, such DNAs can be prepared by:

a) isolating mRNA from suitable cells, for example human embryonic kidney 293 cells or Swiss 3T3 cells, selecting the desired mRNA, for example by hybridisation with a DNA probe or by expression in a suitable expression system and screening for expression of the desired polypeptide, preparing single-stranded cDNA complementary to that mRNA, then double-stranded cDNA therefrom, or b) isolating cDNA from a CDNA library and selecting the desired cDNA, for example using a DNA probe or using a suitable expression system and screening for expression of the desired polypeptide, or c) incorporating the double-stranded DNA of step a) or b) into an appropriate expression vector,
d) transforming appropriate host cells with the vector and isolating the desired DNA.

Polyadenylated messenger RNA (step a) is isolated by known methods. Isolation methods involve, for example, homogenising cells in the presence of a detergent and a ribonuclease inhibitor, for example heparin, guanidinium isothiocyanate or mercaptoethanol, extracting the mRNA with a chloroform-phenol mixture, optionally in the presence of salt and buffer solutions, detergents and/or cation chelating agents, and precipitating mRNA from the remaining aqueous, salt-containing phase with ethanol, isopropanol or the like. The isolated mRNA may be further purified by centrifuging in a caesium chloride gradient followed by ethanol precipitation and/or by chromatographic methods, for example affinity chromatography, for example chromatography on oligo(dT) cellulose or on oligo(U) Sepharose. Preferably, such purified total mRNA is fractionated according to size by gradient centrifugation, for example in a linear sucrose gradient, or chromatography on suitable size fractionation columns, for example on agarose gels.

The desired mRNA is selected by screening the mRNA directly with a DNA probe, or by translation in suitable cells or cell-free systems and screening the obtained polypeptides.

The selection of the desired mRNA is preferably achieved using a DNA hybridisation probe, thereby avoiding the additional step of translation. Suitable DNA probes are DNAs of known nucleotide sequence consisting of at least 17 nucleotides derived from DNAs encoding Ndr or a related kinase.

Synthetic DNA probes are synthesised according to known methods as detailed hereinbelow, preferably by stepwise condensation using the solid phase phosphotriester, phosphite triester or phosphoramidite method, for example the condensation of dinucleotide coupling units by the phosphotriester method. These methods are adapted to the synthesis of mixtures of the desired oligonucleotides by using mixtures of two, three or four nucleotides dA, dC, dG and/or dT in protected form or the corresponding dinucleotide coupling units in the appropriate condensation step as described by Y. Ike et al. (Nucleic Acids Research 11, 477, 1983).

For hybridisation, the DNA probes are labelled, for example radioactively labelled by the well known kinase reaction. The hybridisation of the size-fractionated mRNA with the DNA probes containing a label is performed according to known procedures, i.e. in buffer and salt solutions containing adjuncts, for example calcium chelators, viscosity regulating compounds, proteins, irrelevant DNA and the like, at temperatures favouring selective hybridisation, for example between 0C and 80° C., for example between 25° C. and 50° C. or around 65° C., preferably at around 20° lower than the hybrid double-stranded DNA melting temperature.

Fractionated mRNA may be translated in cells, for example frog oocytes, or in cell-free systems, for example in reticulocyte lysates or wheat germ extracts. The obtained polypeptides are screened for Ndr activity or for reaction with antibodies raised against Ndr or a related kinase, for example in an immunoassay, for example a radioimmunoassay, enzyme immunoassay or immunoassay with fluorescent markers. Such immunoassays and the preparation of polyclonal and monoclonal antibodies are well known in the art and are applied accordingly.

The preparation of a single-stranded complementary DNA (cDNA) from the selected mRNA template is well known in the art, as is the preparation of a double-stranded DNA from a single-stranded DNA. The mRNA template is incubated with a mixture of deoxynucleoside triphosphates, optionally radioactively labelled deoxynucleoside triphosphates (in order to be able to screen the result of the reaction), a primer sequence such as an oligo-dT residue hybridising with the poly(A) tail of the mRNA and a suitable enzyme such as a reverse transcriptase for example from avian myeloblastosis virus (AMV). After degradation of the template mRNA for example by alkaline hydrolysis, the cDNA is incubated with a mixture of deoxynucleoside triphosphates and a suitable enzyme to give a double-stranded DNA. Suitable enzymes are for instance a reverse transcriptase, the Klenow fragment of E. coli DNA polymerase I or T4 DNA polymerase. Usually, a hairpin loop structure formed spontaneously by the single-stranded cDNA acts as a primer for the synthesis of the second strand. This hairpin structure is removed by digestion with S1 nuclease. Alternatively, the 3'-end of the single-stranded DNA is first extended by homopolymeric deoxynucleotide tails prior to the hydrolysis of the mRNA template and the subsequent synthesis of the second cDNA strand.

In the alternative, double-stranded cDNA is isolated from a cDNA library and screened for the desired cDNA (step b). The cDNA library is constructed by isolating mRNA from suitable cells, for example human mononuclear leukocytes or human embryonic epithelial lung cells, and preparing single-stranded and double-stranded cDNA therefrom as described above. This cDNA is digested with suitable restriction endonucleases and incorporated into I phage, for example I charon 4A or I gt11 following established procedures. The cDNA library replicated on nitrocellulose membranes is screened by using a DNA probe as described hereinbefore, or expressed in a suitable expression system and the obtained polypeptides screened for reaction with an antibody specific for the desired Ndr family kinase, for example an antibody specific for Ndr.

A variety of methods are known in the art for the incorporation of double-stranded cDNA into an appropriate vector (step c). For example, complementary homopolymer tracts may be added to the double-stranded DNA and the vector DNA by incubation in the presence of the corresponding deoxynucleoside triphosphates and an enzyme such as terminal deoxynucleotidyl transferase. The vector and double-stranded DNA are then joined by base pairing between the complementary homopolymeric tails and finally ligated by specific joining enzymes such as ligases. Other possibilities are the addition of synthetic linkers to the termini of the double-stranded DNA, or the incorporation of the double-stranded DNA into the vector by blunt- or staggered-end ligation.

The transformation of appropriate host cells with the obtained hybrid vector (step d) and the selection of transformed host cells (step e) are well known in the art. Hybrid vectors and host cells may be particularly suitable for the production of DNA, or for the production of the desired polypeptide.

The isolation of the desired DNA is achieved by methods known in the art, for example extraction with phenol and/or chloroform or glass beads. Optionally, the DNA can be further manipulated for example by treatment with mutagenic agents to obtain mutants, or by digestion with restriction enzymes to obtain fragments, modify one or both termini to facilitate incorporation into the vector.

Vectors.

The cDNA or genomic DNA encoding a native or mutant Ndr family kinase or Calcium Binding Protein (Ndr family kinase/CBP) can be incorporated into vectors for further manipulation. As used herein, vector (or plasmid) refers to discrete elements that are used to introduce heterologous DNA into cells for either expression or replication thereof. Selection and use of such vehicles are well within the skill of the artisan. Many vectors are available, and selection of appropriate vector will depend on the intended use of the vector, i.e. whether it is to be used for DNA amplification or for DNA expression, the size of the DNA to be inserted into the vector, and the host cell to be transformed with the vector. Each vector contains various components depending on its function (amplification of DNA or expression of DNA) and the host cell for which it is compatible. The vector components generally include, but are not limited to, one or more of the following: an origin of replication, one or more marker genes, an enhancer element, a promoter, a transcription termination sequence and a signal sequence.

Both expression and cloning vectors generally contain nucleic acid sequence that enable the vector to replicate in one or more selected host cells. Typically in cloning vectors, this sequence is one that enables the vector to replicate independently of the host chromosomal DNA, and includes origins of replication or autonomously replicating sequences. Such sequences are well known for a variety of bacteria, yeast and viruses. The origin of replication from the plasmid pBR322 is suitable for most Gram-negative bacteria, the 2m plasmid origin is suitable for yeast, and various viral origins (e.g. SV 40, polyoma, adenovirus) are useful for cloning vectors in mammalian cells. Generally, the origin of replication component is not needed for mammalian expression vectors unless these are used in mammalian cells competent for high level DNA replication, such as COS cells.

Most expression vectors are shuttle vectors, i.e. they are capable of replication in at least one class of organisms but can be transfected into another class of organisms for expression. For example, a vector is cloned in E. coli and then the same vector is transfected into yeast or mammalian cells even though it is not capable of replicating independently of the host cell chromosome. DNA may also be replicated by insertion into the host genome. However, the recovery of genomic DNA encoding an Ndr family kinase/CBP is more complex than that of exogenously replicated vector because restriction enzyme digestion is required to excise Ndr family kinase/CBP DNA. DNA can be amplified by PCR and be directly transfected into the host cells without any replication component.

Advantageously an expression and cloning vector may contain a selection gene also referred to as selectable marker. This gene encodes a protein necessary for the survival or growth of transformed host cells grown in a selective culture medium. Host cells not transformed with the vector containing the selection gene will not survive in the culture medium. Typical selection genes encode proteins that confer resistance to antibiotics and other toxins, e.g. ampicillin, neomycin, methotrexate or tetracycline, complement auxotrophic deficiencies, or supply critical nutrients not available from complex media.

As to a selective gene marker appropriate for yeast, any marker gene can be used which facilitates the selection for transformants due to the phenotypic expression of the marker gene. Suitable markers for yeast are, for example, those conferring resistance to antibiotics G418, hygromycin or bleomycin, or provide for prototrophy in an auxotrophic yeast mutant, for example the URA3, LEU2, LYS2, TRP1, or HIS3 gene.

Since the replication of vectors is conveniently done in E. coli, an E. coli genetic marker and an E. coli origin of replication are advantageously included. These can be obtained from E. coli plasmids, such as pBR322, Bluescript© vector or a pUC plasmid, e.g. pUC18 or pUC19, which contain both E. coli replication origin and E. coli genetic marker conferring resistance to antibiotics, such as ampicillin.

Suitable selectable markers for mammalian cells are those that enable the identification of cells competent to take up Ndr family kinase/CBP nucleic acid, such as dihydrofolate reductase (DHFR, methotrexate resistance), thymidine kinase, or genes conferring resistance to G418 or hygromycin. The mammalian cell transformants are placed under selection pressure which only those transformants which have taken up and are expressing the marker are uniquely adapted to survive. In the case of a DHFR or glutamine synthase (GS) marker, selection pressure can be imposed by culturing the transformants under conditions in which the pressure is progressively increased, thereby leading to amplification (at its chromosomal integration site) of both the selection gene and the linked DNA that encodes Ndr family kinase/CBP. Amplification is the process by which genes in greater demand for the production of a protein critical for growth, together with closely associated genes which may encode a desired protein, are reiterated in tandem within the chromosomes of recombinant cells. Increased quantities of desired protein are usually synthesised from thus amplified DNA.

Expression and cloning vectors usually contain a promoter that is recognised by the host organism and is operably linked to Ndr family kinase/CBP nucleic acid. Such a promoter may be inducible or constitutive. The promoters are operably linked to DNA encoding Ndr family kinase/CBP by removing the promoter from the source DNA by restriction enzyme digestion and inserting the isolated promoter sequence into the vector. Both the native Ndr family kinase/CBP promoter sequence and many heterologous promoters may be used to direct amplification and/or expression of Ndr family kinase/CBP DNA. The term "operably linked" refers to a juxtaposition wherein the components described are in a relationship permitting them to function in their intended manner. A control sequence "operably linked" to a coding sequence is ligated in such a way that expression of the coding sequence is achieved under conditions compatible with the control sequences.

Promoters suitable for use with prokaryotic hosts include, for example, the P-lactamase and lactose promoter systems, alkaline phosphatase, the tryptophan (trp) promoter system and hybrid promoters such as the tac promoter. Their nucleotide sequences have been published, thereby enabling the skilled worker operably to ligate them to DNA encoding Ndr family kinase/CBP, using linkers or adaptors to supply any required restriction sites. Promoters for use in bacterial systems will also generally contain a Shine-Delgarno sequence operably linked to the DNA encoding Ndr family kinase/CBP.

Preferred expression vectors are bacterial expression vectors which comprise a promoter of a bacteriophage such as phagex or T7 which is capable of functioning in the bacteria. In one of the most widely used expression systems, the nucleic acid encoding the fusion protein may be transcribed from the vector by T7 RNA polymerase (Studier et al, Methods in Enzymol. 185; 60–89, 1990). In the E. coli BL21 (DE3) host strain, used in conjunction with pET vectors, the T7 RNA polymerase is produced from the λ-lysogen DE3 in the host bacterium, and its expression is under the control of the IPTG inducible lac UV5 promoter. This system has been employed successfully for over-production of many proteins. Alternatively the polymerase gene may be introduced on a lambda phage by infection with an int-phage such as the CE6 phage which is commercially available (Novagen, Madison, USA). other vectors include vectors containing the lambda PL promoter such as PLEX (Invitrogen, NL), vectors containing the trc promoters such as pTrcHisXpress™ (Invitrogen) or pTrc99 (Pharmacia Biotech, SE), or vectors containing the tac promoter such as pKK223-3 (Pharmacia Biotech) or PMAL (new England Biolabs, MA, USA).

Moreover, the Ndr family kinase/CBP gene according to the invention preferably includes a secretion sequence in order to facilitate secretion of the polypeptide from bacterial hosts, such that it will be produced as a soluble native peptide rather than in an inclusion body. The peptide may be recovered from the bacterial periplasmic space, or the culture medium, as appropriate.

Suitable promoting sequences for use with yeast hosts may be regulated or constitutive and are preferably derived from a highly expressed yeast gene, especially a Saccharomyces cerevisiae gene. Thus, the promoter of the TRP1 gene, the ADHI or ADHII gene, the acid phosphatase (PH05) gene, a promoter of the yeast mating pheromone genes coding for the a- or α-factor or a promoter derived from a gene encoding a glycolytic enzyme such as the promoter of the enolase, glyceraldehyde-3-phosphate dehydrogenase (GAP), 3-phospho glycerate kinase (PGK), hexokinase, pyruvate decarboxylase, phosphofructokinase, glucose-6-phosphate isomerase, 3-phosphoglycerate mutase, pyruvate kinase, triose phosphate isomerase, phosphoglucose isomerase or glucokinase genes, the S. cerevisiae GAL 4 gene, the S. pombe nmt 1 gene or a promoter from the TATA binding protein (TBP) gene can be used. Furthermore, it is possible to use hybrid promoters comprising upstream activation sequences (UAS) of one yeast gene and downstream promoter elements including a functional TATA box of another yeast gene, for example a hybrid promoter including the UAS(s) of the yeast PH05 gene and downstream promoter elements including a functional TATA box of the yeast GAP gene (PH05-GAP hybrid promoter). A suitable constitutive PH05 promoter is e.g. a shortened acid phosphatase PH05 promoter devoid of the upstream regulatory elements (UAS) such as the PH05 (−173) promoter element starting at nucleotide −173 and ending at nucleotide −9 of the PH05 gene.

Ndr family kinase/CBP gene transcription from vectors in mammalian hosts may be controlled by promoters derived from the genomes of viruses such as polyoma virus, adenovirus, fowipox virus, bovine papilloma virus, avian sarcoma virus, cytomegalovirus (CMV), a retrovirus and Simian Virus 40 (SV40), from heterologous mammalian promoters such as the actin promoter or a very strong promoter, e.g. a ribosomal protein promoter, and from the promoter normally associated with Ndr family kinase/CBP sequence, provided such promoters are compatible with the host cell systems.

Transcription of a DNA encoding Ndr family kinase/CBP by higher eukaryotes may be increased by inserting an enhancer sequence into the vector. Enhancers are relatively orientation and position independent. Many enhancer sequences are known from mammalian genes (e.g. elastase and globin). However, typically one will employ an enhancer from a eukaryotic cell virus. Examples include the SV40 enhancer on the late side of the replication origin (bp 100–270) and the CMV early promoter enhancer. The enhancer may be spliced into the vector at a position 5′ or 3′ to the Ndr family kinase/CBP DNA, but is preferably located at a site 5′ from the promoter.

Advantageously, a eukaryotic expression vector encoding Ndr family kinase/CBP may comprise a locus control region (LCR). LCRs are capable of directing high-level integration site independent expression of transgenes integrated into host cell chromatin, which is of importance especially where the Ndr family kinase/CBP gene is to be expressed in the context of a permanently-transfected eukaryotic cell line in which chromosomal integration of the vector has occurred, in vectors designed for gene therapy applications or in transgenic animals.

Eukaryotic expression vectors will also contain sequences necessary for the termination of transcription and for stabilising the mRNA. Such sequences are commonly available from the 5′ and 3′ untranslated regions of eukaryotic or viral DNAs or cDNAs. These regions contain nucleotide segments transcribed as polyadenylated fragments in the untranslated portion of the mRNA encoding Ndr family kinase/CBP.

An expression vector includes any vector capable of expressing Ndr family kinase/CBP nucleic acids that are operatively linked with regulatory sequences, such as promoter regions, that are capable of expression of such DNAs. Thus, an expression vector refers to a recombinant DNA or RNA construct, such as a plasmid, a phage, recombinant virus or other vector, that upon introduction into an appropriate host cell, results in expression of the cloned DNA. Appropriate expression vectors are well known to those with ordinary skill in the art and include those that are replicable in eukaryotic and/or prokaryotic cells and those that remain episomal or those which integrate into the host cell genome. For example, DNAs encoding Ndr family kinase/CBP may be inserted into a vector suitable for expression of cDNAs in mammalian cells, e.g. a CMV enhancer-based vector such as pEVRF (Matthias, et al., (1989) *NAR* 17, 6418).

Particularly useful for practising the present invention are expression vectors that provide for the transient expression of DNA encoding Ndr family kinase/CBP in mammalian cells. Transient expression usually involves the use of an expression vector that is able to replicate efficiently in a host cell, such that the host cell accumulates many copies of the expression vector, and, in turn, synthesises high levels of Ndr family kinase/CBP. For the purposes of the present invention, transient expression systems are useful e.g. for identifying Ndr family kinase/CBP mutants, to identify potential phosphorylation sites, or to characterise functional domains of the protein.

Construction of vectors according to the invention employs conventional ligation techniques. Isolated plasmids or DNA fragments are cleaved, tailored, and religated in the form desired to generate the plasmids required. If desired, analysis to confirm correct sequences in the constructed plasmids is performed in a known fashion. Suitable methods for constructing expression vectors, preparing in vitro transcripts, introducing DNA into host cells, and performing analyses for assessing Ndr family kinase/CBP expression and function are known to those skilled in the art. Gene presence, amplification and/or expression may be measured in a sample directly, for example, by conventional Southern blotting, Northern blotting to quantitate the transcription of mRNA, dot blotting (DNA or RNA analysis), or in situ hybridisation, using an appropriately labelled probe which may be based on a sequence provided herein. Those skilled in the art will readily envisage how these methods may be modified, if desired.

The invention is described below, for the purposes of illustration only, in the following examples:

EXAMPLE 1

Calcium-dependent Interaction of Ndr Protein Kinase with Calmodulin

Ndr protein kinase has been cloned from three divergent species, and alignment of the amino acid sequences from these organisms allows an assessment of which regions of the protein are highly conserved and therefor e functionally important (Millward, T. A., et al., (1995) Proc. Natl. Acad. Sci. USA 92, 5022–5026). Several conserved regions outside of the kinase catalytic domain are evident. One of these, in the amino terminal non-catalytic domain, consists of an 25 amino acid sequence (amino acids 62–86 in the sequence of Ndr from human brain) which is highly enriched in positively charged and hydrophobic amino acids. Computer algorithms suggest that this region is α-helical and has a slightly amphipathic character. Such features are typical of peptides that bind to CaM, a ubiquitous and conserved calcium signal transducing protei n.

To test the hypothesis that human Ndr protein kinase might be able to interact with calmodulin, in vitro binding experiments are conducted using CaM-agarose. Initially, purified recombinant Ndr (GST-Ndr) is mixed with CaM-agarose in a buffer either containing or lacking calcium ions; the solid phase is then washed extensively and treated with EGTA to remove free calcium. 2.5 µg of either glutathione-S-transferase (GST) or GST-Ndr is diluted to 0.1 µg/µl in TBS (50 mM Tris-HCl pH 7.5, 100 mM NaCl) containing 0.05% (v/v) Tween 20 and mixed with 20 µl CaM-aga rose (Sigma) equilibrated in the same buffer. Binding reactions and subsequent wash buffers are supplemented with 1 mM $CaCl_2$ or 1 mM EGTA. After mixing at 4° C. for 2 h, the beads are spun down and the supernatant removed and saved. The beads are washed three times for 10 min. with the binding buffer and then eluted for 15 min with 40 µl TBS containing 0.05% Tween 20 and 5 mM EGTA. Equal portions of input, unbound and EGTA-eluted fractions are analysed by immunoblouting as described below.

In the presence of free $Ca^{2+}$, GST-Ndr binds to CaM-agarose and, after washing, can be eluted by removal of $Ca^{2+}$; under the conditions used, ~50% of the input protein bound. In control assays containing EGTA in the binding step, no binding is detectable. $Ca^{2+}$-dependent binding to CaM-agarose is mediated by the Ndr portion of the fusion protein, because GST shows no binding either in the presence or absence of $Ca^{2+}$ ions.

In addition, the ability of untagged Ndr to interact with CaM is investigated. COS-1 cells are transfected with pECE or with derivative plasmids encoding wild-type Ndr, NdrΔ65-81 or NdrΔ1-84 (Millward, T. A., et al., (1995) Proc. Natl. Acad. Sci. USA 92, 5022–5026) using DEAE-dextran (Seed, B. and Aruffo, A. (1987) Proc. Natl. Acad. Sci. USA 84, 3365–3369). Seventy-two hours after transfection, cells are scraped into ice-cold phosphate-buffered saline (PBS), spun down, and disrupted in buffer A (TBS containing 1 mM dithiothreitol, 0.5 mM phenylmethylsulfonyl fluoride, 4 µM leupeptin and 1 mM benzamidine) using a tight-fitting all-glass dounce homogenizer. Extracts (20 µg) are adjusted to 1 mg/ml, supplemented with either 1 mM $CaCl_2$ or 1 mM EGTA and then mixed for 2 h with 6 µl CaM-agarose. After washing three times with 1 ml of the corresponding binding buffer, the beads are eluted with buffer A containing 5 mM EGTA. Equal portions of the unbound and EGTA-eluted fractions are analysed by immunoblofting with anti-Ndr antibodies.

Samples are separated by SDS-PAGE and electroblotted to Immobilon-P membranes (Millipore). Blots are incubated in blocking buffer (50 mM Tris-HCl pH 7.5, 150 mM NaCl, 1% (v/v) Triton X-1 00, 0.5% (v/v) Tween 20, 5% (w/v) skim milk powder) and then probed for 2 h with primary antibodies diluted in the same buffer. Ndr and GST-Ndr are detected with $Ab^{452-465}$ at 4 µg/ml (Millward, T. A., et al., Op. Cit.); GST is detected with an anti-GST antiserum (1 : 1000 dilution). Bound antibodies are detected using horseradish peroxidase-conjugated donkey anti-rabbit IgG antibodies and ECL substrates (Amersham).

In lysates supplemented with $Ca^{2+}$, Ndr is quantitatively and selectively removed from the lysate by CaM-agarose, and can be eluted subsequently with EGTA. In contrast, no detectable binding occurs when the lysate is supplemented with EGTA. These results indicate that Ndr protein kinase is capable of $Ca^{2+}$-dependent and reversible binding to CaM. The Amino Terminal Non-catalytic Domain of Ndr Protein Kinase Mediates Interaction with Calmodulin The idea to test whether Ndr could interact with CaM had been suggested by the presence of a basic/hydrophobic putative a-helical region in the amino terminal domain of Ndr (see above). To verify whether this domain of Ndr is indeed responsible for its interaction with CaM, deletion mutants of Ndr are expressed in COS-1 cells and tested for CaM binding as above. The deletions tested encompassed the complete amino terminal domain of Ndr (Δ1-84) and a 17 amino acid region within the putative CaM-binding sequence (Δ65-81). In lysates supplemented with $Ca^2$, deletion of amino acids 65-81 cause a large reduction in CaM binding (to ~10% of the level of wild-type binding) as assessed by western blotting. When the complete amino terminal domain of Ndr is removed, binding to CaM-agarose is no longer detectable.

In immune complex kinase assays and autophosphorylation assays (see below), COS-1 cells are transfected as described above or with pECE-Ndr-K118A. After 72 h, cells are washed with ice-cold PBS and lysed in lysis buffer (20 mM Tris-HCl pH 8.0, 150 mM NaCl, 1% (v/v) NP-40, 10% (v/v) glycerol, 5 mM EDTA, 0.5 mM EGTA, 0.5 mM phenylmethyl-sulfonyl fluoride, 4 µM leupeptin, 1 mM benzamidine, 1 µM microcystin and 1 mM $Na_3VO_4$). Lysates are centrifuged at 14,000 g for 20 min. Duplicate aliquots of supernatant (250 µg, 2.5 mg/ml) are incubated for 2 h at 0° C. with 10 µg/ml $Ab^{1-465}$. Immune complexes are precipitated by addition of 2 µl protein A-Sepharose (Pharmacia) and mixing for 1 h. The beads are then washed twice with lysis buffer, once with lysis buffer containing 1 M NaCl, with lysis buffer again, and finally twice with 20 mM Tris-HCl pH 7.5. Beads are resuspended in 30 µl buffer containing 20 mM Tris-HCl pH 7.5, 10 mM $MgCl_2$, 100 µM $CaCl_2$, 1 mM dithiothreitol, 100 µM [$\gamma$-$^{32}$P] ATP (0.5 µCi/µls), 1 mM Ndr substrate peptide (KKRNRRLSVA, SEQ. ID. No. 1), 1 µM cAMP-dependent protein kinase inhibitor peptide (PKI; purchased from Bachem, Bubendorf, Swit zerland), 4 µM leupeptin, 1 mM benzamidine, 1 µM microcystin and, in some assays, 20 µM bovine S100B. After 60 min at 30° C., phosphate incorporation into the peptide is quantitated as described above.

The Δ65-81 mutant shows identical basal kinase activity to the wild-type Ndr protein; using the Δ1-84 mutant, these activities are only slightly reduced. Thus, deletions in the amino terminal domain of Ndr do not cause major changes in the conformation of thete rest of the polypeptide. These results suggest that the amino-terminal domain of Ndr is required for interaction with CaM, and that the CaM binding site overlaps with or is close to amino acids 65–81.

EXAMPLE 2

An Ndr Protein Kinase Assay

When incubated in vitro with Mg-ATP, Ndr incorpora tes phosphate by an intramolecular autophosphorylation mechanism (Millward, T. A., et al., (1995) Proc. Natl. Acad. Sci. USA 92, 5022–5026). However, no protein has been identified that can serve as a substrate for Ndr in transphosphorylation reactions; proteins typically used in kinase assays, such as histone, myelin basic protein, casein and phosvitin are not substrates of Ndr. To develop a convenient in vitro kinase assay for Ndr, an assembled library of synthetic peptides is screened for potential Ndr substrates. 5 μg GST-Ndr WT or GST-Ndr K118A (Miliward, T. A., et al., (1995) Proc. Natl. Acad. Sci. USA 92, 5022–5026), immobilised on 2.5 μl glutathione-agarose beads (Sigma), is assayed in a 25 μl reaction containing 50 mM Tris-HCl pH 7.5, 10 MM $MgCl_2$, 1 mM dithiothreitol, 100 μM [γ-$^{32}$P] ATP (0.3 μCi/μl) and 0.5 mg/ml peptide. After incubation at 3 h at 30° C. (during which time phosphate incorporation into peptides is linear), aliquots of the reaction are spotted onto 2 cm² squares of P81 phosphocellulose paper (Whatman), which are then washed 5×5 min in 1% phosphoric acid and once in acetone, before counting in a liquid scintillation counter.

Several peptides are identified which could serve as Ndr substrates (Table 1; SEQ. ID. No. 1 to 31). By comparing the efficiency of phosphorylation of the various peptides, several conclusions regarding the substrate specificity of Ndr can be drawn. Firstly, comparison of peptides suggested that Ndr uses serine, but not threonine, as the phosphoacceptor. Secondly, most of the peptides which are detectably phosphorylated contained a basic amino acid at position −6 relative to the phosphoaccepting serine. A positive charge at this position appeared to be important for Ndr substrate recognition, because peptides containing an alanine substitution at this position failed to be phosphorylated. Peptide 2 in Table 1, however, shows 39% activity. A basic amino acid at −6 is however not sufficient for substrate recognition, since this peptide is also not phosphorylated. Thirdly, a basic residue at −5 appeared to be also important, although not essential, for efficient phosphorylation by Ndr. Basic amino acids at −3, −2 and −7 are also important. Proline at +1 appears to be inhibitory, whilst the presence of amino acids carboxy-terminal to the phosphoacceptor is important, removal of the residue at +2 reducing activity. The best Ndr substrate from these series of peptides is (KKRNRRLSVA, SEQ. ID. No. 1), and this peptide is used for Ndr kinase assays in subsequent experiments.

TABLE 1

| Peptide Substrate | SEQ. ID. No. | Relative Ndr Activity |
|---|---|---|
| KKRNRRLSVA | 1 | 100% |
| KARNRRLSVA | 2 | 39% |
| KKLNRRLSVA | 3 | 18% |
| KKRNARLSVA | 4 | 15% |
| KKRNRALSVA | 5 | 30% |
| KKRNRTLSVA | 6 | 60% |
| AARNRTLSVA | 7 | 0% |
| KKRNRTLSPA | 10 | 0% |
| KKRNRTLSV | 8 | 24% |
| KKRNRTLTV | 9 | 0% |

Amino acids mutated from the KKRNRRLSVA peptide (SEQ. ID. No. 1) are underlined; the phosphoacceptor serine residue is shown in bold.

EXAMPLE 3

Activation of Ndr Protein Kinase by the CaM-related Proteins S100B and S100A1

Because several protein kinases are known that are activated by direct interaction with $Ca^{2+}$-CaM, it is tested whether the kinase activity of Ndr is regulated by binding to CaM.

1 μg GST-Ndr WT or GST-Ndr K118A, either in solution or immobilised on glutathione-agarose beads, is assayed in a 20 μl reaction containing 20 mM Tris-HCl pH 7.5, 5 mM $MgCl_2$, 1 mM dithiothreitol, 100 μM [γ-$^{32}$P] ATP (0.25 μCi/μl) and 1 mM Ndr substrate peptide (KKRNRRLSVA, SEQ. ID. No. 1). Reactions are supplemented with either 2 mM EGTA or various concentrations of $CaCl_2$. Bovine CaM, bovine S100B (both from Sigma) or recombinant calcium-binding proteins. After incubation at 30° C. for 60 min, aliquots of the reaction are spotted on to P81 phosphocellulose paper and counted as above.

In peptide kinase assays and autophosphorylation assays, $Ca^{2+}$-CaM has only a minor effect (<2-fold activation) on Ndr kinase activity. CaM is, however, a member of a large family of calcium-binding proteins, which share conserved structural features and a common mechanism of action. One subclass of $Ca^{2+}$-binding proteins are the S100 proteins (Schafer, B. W. and Heizmann, C. W. (1996) Trends Biochem. Sci. 21, 134–140). These are acidic, low molecular weight dimeric proteins which, like CaM, bind $Ca^{2+}$ through EF hand motifs and undergo a $Ca^{2+}$-induced conformational change to expose a hydrophobic effector protein binding surface (Smith, S. P. et al., (1996) Biochemistry 35, 8805–8814). In many cases S100 proteins have been found to bind target sequences that are similar or identical to those bound by CaM (Ivanenkov, V. V., et al., (1995) J. Biol. Chem. 270, 14651–14658; Baudier, J., et al., (1987) Biochemistry 26, 2886–2893). Furthermore, CaM and S100 proteins can have differential effects on the same enzyme, even when they bind to the same site (Heierhorst, J., et al., (1996) Nature 380, 636–639; Baudier, J., et al., (1995) Biochemistry 34, 7834–7846).

To investigate whether S1 00 proteins might functionally interact with Ndr, several members of the S100 protein family are screened for modulation of Ndr protein kinase activity. These proteins are expressed from cloned cDNAs in E. coli, purified following a standard protocol.

In brief, coding regions are cloned into the PGEMEX expression vector (Promega) and resultant plasmids used to transform E. coli BL-21 LysS cells. After induction, S100 proteins are purified by ammonium sulphate precipitation followed by $Ca^{2+}$-dependent phenyl-Sepharose chromatography. Parvalbumin is purified by ion-exchange chromatography on Q Sepharose (Rhyner, J. A., et al., (1 996) Biochim. Biophys. Acta 1313, 179–186). All purified proteins are homogeneous as judged by SDS-PAGE and Coomassie blue staining.

The proteins are added together with $Ca^{2+}$ into GST-N dr peptide kinase assays. The proteins tested comprised S100A1 (S100α), S100A2 (S100L), S100A4 (CAPL), S100A6 (calcyclin) and S100B (S100β); α-parvalbumin is included as a negative control. Most of these proteins, like CaM, have little or no effect on the activity of Ndr. However, one protein, S100B, causes a 5- to 6-fold increase in Ndr kinase activity. S100B also stimulated Ndr autophosphorylation. A smaller (2- to 3-fold) activation is observed with S100A1, which is phylogenetically the closest known relative of S100B. The increased kinase activity observed in the presence of S100A1 and S100B is not due to contaminating kinase activity, because no activity is recorded when kinase-negative GST-Ndr, containing a point mutation ($Lys^{118}$→Ala) in the ATP binding pocket, is used in place of wild-type GST-Ndr. Thus, Ndr can be activated in vitro by S100B and to a lesser extent by S100Ai.

EXAMPLE 4

Calcium and S100 B Dependence of Ndr Activation

Because S100B is found to be the strongest activator of Ndr, subsequent experiments are focused on further characterisation of Ndr activation by this protein. In order to estimate the binding affinity of S100B for Ndr, kinase assays are performed in which GST-Ndr is mixed with various concentrations of purified bovine S100B homodimer, in the presence or absence of calcium. The maximal activation of Ndr by $Ca^{2+} \rightarrow S100B$ is ~7-fold, and the concentration of $Ca^{2+}$-S100B required for half-maximal activation ($EC_{50}$) is ~1 μM. Surprisingly, apo-S100B (assayed in the presence of 2 mM EGTA) also caused some activation of Ndr, although maximal activation is much lower, and the $EC_{50}$ appears to be significantly higher (~10 μM). In fact, S100B may exhibit a reduced calcium requirement because similar phenomena have been observed previously: for example, myosin heavy chain, fructose-1,6-bisphosphate aldolase and glycogen phosphorylase all show strictly $Ca^{2+}$-dependent binding to CaM but partially $Ca^{2+}$-independent binding to S100B in gel overlay experiments.

To determine whether activation of Ndr by S100B occurs at physiological $Ca^{2+}$ concentrations, Ndr activity is assayed with or without added S100B over a range of $Ca^{2+}$ concentrations. Ndr per se shows no $Ca^{2+}$ sensitivity; however, in the presence of 10 μM S100B a $Ca^{2+}$ regulated activation of Ndr is observed. The $Ca^{2+}$-dependent component of this activation is most responsive to $Ca^{2+}$ concentrations in the range of 1–100 μM. This is in good agreement with previous estimates of the $K_d$ of S100B for $Ca^{2+}$. At supraphysiological concentrations of $Ca^{2+}$ (>100 μM), a slight reduction in activation is seen. As noted above, S100B also causes partial activation of Ndr in the absence of calcium.

Activation of Ndr by S100B appears to be independent of kinase autophosphorylation. However, increased autophosphorylation is observed: GST-Ndr is immobilised on agarose and preincubated with or without $Ca^{2+}$-S100B, in the presence or absence of Mg-ATP (to either allow or not allow autophosphorylation). The agarose beads are then washed and assayed for Ndr activity as set out herein with radiolabelled ATP and peptide substrate, and in the presence or absence of $Ca^{2+}$-S100B. Preincubation of GST-Ndr with Mg-ATP alone increases its peptide kinase activity, showing that autophosphorylation activates Ndr. Preincubation of GST-Ndr with Mg-ATP and $Ca^{2+}$-S100B results in an even greater autoactivation of the peptide kinase activity; this is as expected, since S100B increases Ndr autophosphorylation. Preincubation with $Ca^{2+}$S100B alone has no effect, because activation by $Ca^{2+}$-S100B in the preincubation step is mediated by Ndr autophosphorylation.

$Ca^{2+}$-S100B increases the rate Ndr autophosphorylation by 2.5-fold, and it increases autophosphorylation-dependent Ndr activation by 2-fold. However, the total activation of Ndr by $Ca^{2+}$-S100B is larger than this (5- to 10-fold). Thus, the increased autophosphorylation of Ndr caused by $Ca^{2+}$-S100B is not by itself sufficient to account for Ndr activation. In addition, $Ca^{2+}$-S100B probably stimulates Ndr kinase activity directly, in an autophosphorylation-independent manner.

EXAMPLE 5

S100B-dependent Activation of Ndr in Response to Elevation of Intracellular Calcium In order to provide direct evidence that $Ca^{2+}$/S100B regulates Ndr activity in vivo, COS-1 cells are co-transfected with expression constructs for Ndr and S100B (pECE-HA-Ndr, which expresses haemaglutinin epitope-tagged Ndr from an SV40 promoter, and pECE-S100B). Two Ndr constructs are used, expressing either wild-type Ndr (Ndr WT) or Ndr lacking the previously identified S100B binding domain (Ndr Δ65-81). Then, the cells are treated for various lengths of time with 20 μM A23187, a calcium ionophore. The resultant elevation of intracellular calcium concentration leads to activation of HA-Ndr WT (measured by immunoprecipitating the kinase with the 12CA5 monoclonal antibody and measuring its ability to phosphorylate the peptide KKRNRRLSVA (SEQ ID No. 1) but not of HA-Ndr Δ65-81. This provides direct evidence that elevation of intracellular calcium activates Ndr in vivo and that this activation is mediated by S100B. Anti-HA immunoblots (using mAb 12CA5) of the cell extracts show that both Ndr constructs are expressed at the same level, and that expression level is not changed by calcium ionophore treatment.

EXAMPLE 6

Activation of Ndr by S100B Requires the Identified CaM Binding Domain of Ndr

As described above, S100 proteins and CaM often seem to have similar binding specificities for interaction with their effector proteins. According to this model, deletion mutants of Ndr lacking the CaM binding sequences should also fail to be activated by S100B.

To test this hypothesis, amino terminal deletion mutants of Ndr are expressed in COS-1 cells, and then subjected to an immune complex kinase assay in the presence or absence of exogenously added S100B and $Ca^{2+}$. Immunoprecipitated wild-type Ndr is also activated by $Ca^{2+}$-S100B. The degree of activation in these assays is somewhat lower than with GST-Ndr (only ~2-fold), most likely because antibodies in the immune complex restricted access of S100B to its binding site. Nevertheless, deletion of amino acids 65–81 of Ndr ablated its sensitivity to S100B without having any effect on basal Ndr activity. Ndr lacking the entire amino terminal domain (Δ1-84) also failed to respond to S100B, and had a reduced basal kinase activity. Therefore, the basic/hydrophobic region in the amino terminal domain of Ndr is required for activation of Ndr by S100B.

EXAMPLE 7

Overexpression of S100B Causes Hyperactivation of Ndr

A panel of 12 melanoma cell lines are analysed for S100B expression, Ndr expression and Ndr activity using anti-Ndr specific antibodies. These cell lines comprise two human carcinoma cell lines (HeLa and HEY), nine human melanoma cell lines (M14, Sk29, A375, CaCL 74-36, CaCL 78-1, Me15, G361, M960618 and M961205), and a rat glioma cell line (C6).

COS cells are transfected with pECE-Ndr or with empty vector (pECE). 20 μg of these extracts are immunoprecipitated with anti-Ndr (which has been covalently cross-linked to protein A-Sepharose using dimethyl pimelimidate). 400 μg of extract from HeLa cells is immunoprecipitated in parallel. The immunoprecipitates are separated by SDS-PAGE and then immunoblotted using biotinylated anti-Ndr and streptavidin-peroxidase. This procedure reveals a protein of ~55 kDa in HeLa cells that co-migrates with the product of the Ndr cDNA expressed in COS-1 cells. A band of ~53 kDa is also present in HeLa and COS-1 cells and probably represents a proteolytic fragment of full-length Ndr.

Using the method described above, the 12 cell lines are analysed for Ndr abundance. The amount of Ndr (in ng per 400 μg cell extract) is quantitated by densitometry of the blots, and comparison with blots containing known amounts of GST-Ndr. The same cell lines are also assayed for the presence or absence of S100B, by immunoprecipitation of cell extracts with anti-S100B, followed by immunoblotting of the precipitates.

The activity of Ndr in each cell line is measured by immunoprecipitating 400 μg of each extract (in duplicate)

using anti-Ndr, and then measuring the peptide kinase activity of each precipitate (as in Example 5).

A positive correlation is found to exist between Ndr specific activity and S100B expression. In cells expressing high levels of S100B, the average specific activity among the S100B-positive cell lines is ~2-fold higher than among S100B-negative cell lines. This difference is statistically significant (p<0.05) using a two-tailed Students' t test. Accordingly, Ndr is hyperactivated in melanoma cell lines supporting the hypothesis that S100B overexpression can lead to hyperactivation of Ndr.

To further test this hypothesis, the effects of W-7 on Ndr activity are examined in an S100B-positive melanoma line (M960618) in comparison to an S100B-negative melanoma line (A375). W-7 was originally identified as a cell-permeable inhibitor of CaM, which binds to CaM in a $Ca^{2+}$-dependent manner and antagonises the interaction of CaM with its target proteins (Hidaka et al., (1981) *Proc. Natl. Acad. Sci. USA,* 78, 4354–4357; Hidaka and Tanaka, (1983) *Methods Enzymol.,* 102, 185–194). However, W-7 also binds to several S100 proteins, including S100B, in a $Ca^{2+}$-dependent manner (Umekawa et al., (1983) *Arch. Biochem. Biophys.,* 227, 147–153; Todoroki et al., (1991) *J. Biol. Chem.,* 266, 18668–18673) and thus would be expected to antagonise S100 proteins in the same way as CaM.

Treatment of S100B-negative A375 melanoma cells with W-7 (50 µM, 75 minutes) does not affect Ndr activity. In contrast, the same treatment in M960618 melanoma cells (which are S100B-positive and have elevated Ndr activity) reduces Ndr activity by ~80%, to a level similar to that present in A375 cells. These results indicate that S100B overexpression not only correlates with but is indeed the cause of Ndr hyperactivation in S100B-positive melanoma cells.

EXAMPLE 8
Complex Formation Between Ndr and S100B in vivo

For expression of Ndr and S100B in mammalian cells, the cDNAs encoding Ndr and S100B are cloned into the pECE vector, which directs expression driven by an SV40-derived promoter. In addition, an amino-terminal truncation mutant of Ndr lacking the first 84 amino acids (1–84) is used.

The plasmids encoding Ndr and S100B are transfected into COS-1 cells, either alone or in combination. Seventy-two hours later, cells extracts are prepared and immunoprecipitated with an antibody recognising S100B. In an anti-Ndr western blot of the cell extracts, it is shown that Ndr is expressed an expected. In an anti-Ndr western blot of the anti-S100B immunoprecipitates, it is shown that when Ndr and S100B are co-expressed, anti-S100B antibodies co-immunoprecipitated Ndr, indicating that Ndr and S100B are complexed in the cell lysate. This complex formation is specific because deletion of the amino terminal domain of Ndr abolishes co-immunoprecipitation.

EXAMPLE 9
Negative Regulation of Ndr by Protein Phosphatase 2A

The following results provide the first evidence that Ndr is negatively regulated by protein phosphatase 2A (PP2A), a phosphoserine/phosphothreonine phosphatase.

COS-1 cells expressing HA-Ndr WT (as in Example 5) are treated either with solvent alone (Control) or with a panel of cell permeable protein phosphatase inhibitors. The cells are then extracted, HA-Ndr is immunoprecipitated with the anti-HA mAb 12CA5, and the kinase activity of Ndr measured as before, using the peptide substrate. Treatment of cells with 1 µM okadaic acid for 1 h activates Ndr by ~8-fold, while treatment with 10 nM calyculin A for 1 h causes a ~4-fold activation. Treatment with 1 µM cyclosporin A for 1 h has no effect.

Previous studies (Favre, B., et al., (1997), *J. Bio. Chem.* 272, 13856–13863) have shown that, when applied to cells at the concentrations used above, okadaic acid completely inhibits intracellular PP2A but does not affect protein phosphatase 1 (PP1), whereas calyculin A causes a ~50% inhibition of both PP2A and PP1. Cyclosporin A inhibits protein phosphatase 2B (calcineurin) without affecting PP2A or PP1. Therefore, the activation profile of Ndr by the various inhibitors strongly indicates that Ndr is negatively regulated by PP2A but not by PP1 or calcineurin.

In order to provide evidence that PP2A directly interacts with and thereby affects Ndr activity, HA-Ndr is immunoprecipitated from cells treated with 20 µM A23187 or with solvent alone for 5 min. In parallel, HA-Ndr is immunoprecipitated from cells treated with 1 µM okadaic acid or solvent alone ("Control") for 1 h. Each immunoprecipitate is then incubated in vitro for 1 h with either buffer alone, with purified PP2A (dimeric form consisting of catalytic subunit and 65 kDa regulatory subunit) or with PP2A plus 100 nM okadaic acid. Thereafter, the immunoprecipitates are washed and assayed for Ndr peptide kinase activity as described in Example 5. HA-Ndr from control, okadaic acid-, or A23187-treated cells is completely inactivated by incubation with PP2A. This inactivation is prevented by inclusion of okadaic acid in the reaction buffer, demonstrating that inactivation of Ndr is caused specifically by the phosphatase activity of PP2A.

These results show that PP2A is able to directly dephosphorylate and inactivate Ndr. Moreover, it shows that the kinase activity of Ndr is dependent upon its phosphorylation status, and that both okadaic acid and A23187 cause Ndr activation by increasing its phosphorylation status. This confirms previous assumptions: cell treatment with okadaic acid increases Ndr phosphorylation by inhibiting PP2A; cell treatment with A23187 increases Ndr phosphorylation by stimulating association of Ndr with S100B, which stimulates Ndr to autophosphorylate.

SEQUENCE LISTING

```
<160> NUMBER OF SEQ ID NOS:  34

<210> SEQ ID NO 1
<211> LENGTH: 10
<212> TYPE: PRT
<213> ORGANISM: Artificial Sequence
<220> FEATURE:
<223> OTHER INFORMATION: Description of Artificial Sequence:synthetic
```

```
         peptide
<223> OTHER INFORMATION: internal fragment

<400> SEQUENCE: 1

Lys Lys Arg Asn Arg Arg Leu Ser Val Ala
 1               5                  10

<210> SEQ ID NO 2
<211> LENGTH: 10
<212> TYPE: PRT
<213> ORGANISM: Artificial Sequence
<220> FEATURE:
<223> OTHER INFORMATION: Description of Artificial Sequence:synthetic
      peptide
<223> OTHER INFORMATION: internal peptide

<400> SEQUENCE: 2

Leu Ala Arg Asn Arg Arg Leu Ser Val Ala
 1               5                  10

<210> SEQ ID NO 3
<211> LENGTH: 10
<212> TYPE: PRT
<213> ORGANISM: Artificial Sequence
<220> FEATURE:
<223> OTHER INFORMATION: Description of Artificial Sequence:synthetic
      peptide
<223> OTHER INFORMATION: internal peptide

<400> SEQUENCE: 3

Lys Lys Leu Asn Arg Arg Leu Ser Val Ala
 1               5                  10

<210> SEQ ID NO 4
<211> LENGTH: 10
<212> TYPE: PRT
<213> ORGANISM: Artificial Sequence
<220> FEATURE:
<223> OTHER INFORMATION: Description of Artificial Sequence:synthetic
      peptide
<223> OTHER INFORMATION: internal peptide

<400> SEQUENCE: 4

Lys Lys Arg Asn Ala Arg Leu Ser Val Ala
 1               5                  10

<210> SEQ ID NO 5
<211> LENGTH: 10
<212> TYPE: PRT
<213> ORGANISM: Artificial Sequence
<220> FEATURE:
<223> OTHER INFORMATION: Description of Artificial Sequence:synthetic
      peptide
<223> OTHER INFORMATION: internal peptide

<400> SEQUENCE: 5

Lys Lys Arg Asn Arg Ala Leu Ser Val Ala
 1               5                  10

<210> SEQ ID NO 6
<211> LENGTH: 10
<212> TYPE: PRT
<213> ORGANISM: Artificial Sequence
<220> FEATURE:
<223> OTHER INFORMATION: internal peptide
<223> OTHER INFORMATION: Description of Artificial Sequence:synthetic
      peptide

<400> SEQUENCE: 6
```

Lys Lys Arg Asn Arg Thr Leu Ser Val Ala
 1               5                  10

<210> SEQ ID NO 7
<211> LENGTH: 10
<212> TYPE: PRT
<213> ORGANISM: Artificial Sequence
<220> FEATURE:
<223> OTHER INFORMATION: Description of Artificial Sequence:synthetic
      peptide
<223> OTHER INFORMATION: internal peptide

<400> SEQUENCE: 7

Ala Ala Arg Asn Arg Thr Leu Ser Val Ala
 1               5                  10

<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence:synthetic
      peptide
<223> OTHER INFORMATION: internal peptide

<400> SEQUENCE: 8

Lys Lys Arg Asn Arg Thr Leu Ser Val
 1               5

<210> SEQ ID NO 9
<211> LENGTH: 9
<212> TYPE: PRT
<213> ORGANISM: Artificial Sequence
<220> FEATURE:
<223> OTHER INFORMATION: Description of Artificial Sequence:synthetic
      peptide
<223> OTHER INFORMATION: internal peptide

<400> SEQUENCE: 9

Lys Lys Arg Asn Arg Thr Leu Thr Val
 1               5

<210> SEQ ID NO 10
<211> LENGTH: 10
<212> TYPE: PRT
<213> ORGANISM: Artificial Sequence
<220> FEATURE:
<223> OTHER INFORMATION: Description of Artificial Sequence:synthetic
      peptide
<223> OTHER INFORMATION: internal peptide

<400> SEQUENCE: 10

Lys Lys Arg Asn Arg Thr Leu Ser Pro Ala
 1               5                  10

<210> SEQ ID NO 11
<211> LENGTH: 10
<212> TYPE: PRT
<213> ORGANISM: Artificial Sequence
<220> FEATURE:
<223> OTHER INFORMATION: Description of Artificial Sequence:synthetic
      peptide
<223> OTHER INFORMATION: internal peptide

<400> SEQUENCE: 11

Lys Lys Leu Asn Arg Thr Leu Ser Val Ala
 1               5                  10

```
<210> SEQ ID NO 12
<211> LENGTH: 10
<212> TYPE: PRT
<213> ORGANISM: Artificial Sequence
<220> FEATURE:
<223> OTHER INFORMATION: Description of Artificial Sequence:synthetic
      peptide
<223> OTHER INFORMATION: internal peptide

<400> SEQUENCE: 12

Lys Lys Pro Asn Arg Thr Leu Ser Val Ala
 1               5                  10

<210> SEQ ID NO 13
<211> LENGTH: 10
<212> TYPE: PRT
<213> ORGANISM: Artificial Sequence
<220> FEATURE:
<223> OTHER INFORMATION: Description of Artificial Sequence:synthetic
      peptide
<223> OTHER INFORMATION: internal peptide

<400> SEQUENCE: 13

Lys Lys Glu Asn Arg Thr Leu Ser Val Ala
 1               5                  10

<210> SEQ ID NO 14
<211> LENGTH: 10
<212> TYPE: PRT
<213> ORGANISM: Artificial Sequence
<220> FEATURE:
<223> OTHER INFORMATION: Description of Artificial Sequence:synthetic
      peptide
<223> OTHER INFORMATION: internal peptide

<400> SEQUENCE: 14

Lys Lys Lys Asn Arg Thr Leu Ser Val Ala
 1               5                  10

<210> SEQ ID NO 15
<211> LENGTH: 10
<212> TYPE: PRT
<213> ORGANISM: Artificial Sequence
<220> FEATURE:
<223> OTHER INFORMATION: Description of Artificial Sequence:synthetic
      peptide
<223> OTHER INFORMATION: internal peptide

<400> SEQUENCE: 15

Ala Ala Lys Asn Arg Thr Leu Ser Val Ala
 1               5                  10

<210> SEQ ID NO 16
<211> LENGTH: 10
<212> TYPE: PRT
<213> ORGANISM: Artificial Sequence
<220> FEATURE:
<223> OTHER INFORMATION: Description of Artificial Sequence:synthetic
      peptide
<223> OTHER INFORMATION: internal peptide

<400> SEQUENCE: 16

Lys Lys Leu Arg Arg Thr Leu Ser Val Ala
 1               5                  10

<210> SEQ ID NO 17
<211> LENGTH: 9
<212> TYPE: PRT
```

```
<213> ORGANISM: Artificial Sequence
<220> FEATURE:
<223> OTHER INFORMATION: Description of Artificial Sequence:synthetic
      peptide
<223> OTHER INFORMATION: internal peptide

<400> SEQUENCE: 17

Arg Arg Arg Arg Ala Ala Ser Val Ala
 1               5

<210> SEQ ID NO 18
<211> LENGTH: 11
<212> TYPE: PRT
<213> ORGANISM: Artificial Sequence
<220> FEATURE:
<223> OTHER INFORMATION: Description of Artificial Sequence:synthetic
      peptide
<223> OTHER INFORMATION: internal peptide

<400> SEQUENCE: 18

Gln Lys Arg Pro Ser Gln Arg Ser Lys Tyr Leu
 1               5                  10

<210> SEQ ID NO 19
<211> LENGTH: 10
<212> TYPE: PRT
<213> ORGANISM: Artificial Sequence
<220> FEATURE:
<223> OTHER INFORMATION: Description of Artificial Sequence:synthetic
      peptide
<223> OTHER INFORMATION: internal peptide

<400> SEQUENCE: 19

Lys Lys Arg Asn Lys Thr Leu Ser Val Ala
 1               5                  10

<210> SEQ ID NO 20
<211> LENGTH: 13
<212> TYPE: PRT
<213> ORGANISM: Artificial Sequence
<220> FEATURE:
<223> OTHER INFORMATION: Description of Artificial Sequence:synthetic
      peptide
<223> OTHER INFORMATION: internal peptide

<400> SEQUENCE: 20

Arg Phe Ala Arg Lys Gly Ser Leu Arg Gln Lys Asn Val
 1               5                  10

<210> SEQ ID NO 21
<211> LENGTH: 10
<212> TYPE: PRT
<213> ORGANISM: Artificial Sequence
<220> FEATURE:
<223> OTHER INFORMATION: Description of Artificial Sequence:synthetic
      peptide
<223> OTHER INFORMATION: internal peptide

<400> SEQUENCE: 21

Lys Lys Leu Asn Lys Thr Leu Ser Val Ala
 1               5                  10

<210> SEQ ID NO 22
<211> LENGTH: 7
<212> TYPE: PRT
<213> ORGANISM: Artificial Sequence
<220> FEATURE:
<223> OTHER INFORMATION: Description of Artificial Sequence:synthetic
      peptide
```

```
<223> OTHER INFORMATION: internal peptide

<400> SEQUENCE: 22

Leu Arg Arg Ala Ser Val Ala
 1               5

<210> SEQ ID NO 23
<211> LENGTH: 7
<212> TYPE: PRT
<213> ORGANISM: Artificial Sequence
<220> FEATURE:
<223> OTHER INFORMATION: Description of Artificial Sequence:synthetic
      peptide
<223> OTHER INFORMATION: internal peptide

<400> SEQUENCE: 23

Leu Arg Arg Ala Ser Leu Gly
 1               5

<210> SEQ ID NO 24
<211> LENGTH: 9
<212> TYPE: PRT
<213> ORGANISM: Artificial Sequence
<220> FEATURE:
<223> OTHER INFORMATION: Description of Artificial Sequence:synthetic
      peptide
<223> OTHER INFORMATION: internal peptide

<400> SEQUENCE: 24

Arg Pro Pro Gly Phe Ser Pro Phe Arg
 1               5

<210> SEQ ID NO 25
<211> LENGTH: 8
<212> TYPE: PRT
<213> ORGANISM: Artificial Sequence
<220> FEATURE:
<223> OTHER INFORMATION: Description of Artificial Sequence:synthetic
      peptide

<400> SEQUENCE: 25

Arg Arg Leu Ser Ser Leu Arg Ala
 1               5

<210> SEQ ID NO 26
<211> LENGTH: 11
<212> TYPE: PRT
<213> ORGANISM: Artificial Sequence
<220> FEATURE:
<223> OTHER INFORMATION: Description of Artificial Sequence:synthetic
      peptide
<223> OTHER INFORMATION: internal peptide

<400> SEQUENCE: 26

Gly Arg Pro Arg Thr Ser Ser Phe Ala Glu Gly
 1               5                  10

<210> SEQ ID NO 27
<211> LENGTH: 14
<212> TYPE: PRT
<213> ORGANISM: Artificial Sequence
<220> FEATURE:
<223> OTHER INFORMATION: Description of Artificial Sequence:synthetic
      peptide
<223> OTHER INFORMATION: internal peptide

<400> SEQUENCE: 27

Thr Ala Arg Gly Ala Ile Pro Ser Tyr Met Lys Ala Ala Lys
```

<210> SEQ ID NO 28
<211> LENGTH: 11
<212> TYPE: PRT
<213> ORGANISM: Artificial Sequence
<220> FEATURE:
<223> OTHER INFORMATION: Description of Artificial Sequence:synthetic
      peptide
<223> OTHER INFORMATION: internal peptide

<400> SEQUENCE: 28

Ala Lys Ala Lys Lys Thr Pro Lys Lys Ala Lys
 1               5                  10

<210> SEQ ID NO 29
<211> LENGTH: 11
<212> TYPE: PRT
<213> ORGANISM: Artificial Sequence
<220> FEATURE:
<223> OTHER INFORMATION: Description of Artificial Sequence:synthetic
      peptide
<223> OTHER INFORMATION: internal peptide

<400> SEQUENCE: 29

Ala Lys Ala Lys Lys Thr Gly Lys Lys Ala Lys
 1               5                  10

<210> SEQ ID NO 30
<211> LENGTH: 13
<212> TYPE: PRT
<213> ORGANISM: Artificial Sequence
<220> FEATURE:
<223> OTHER INFORMATION: Description of Artificial Sequence:synthetic
      peptide
<223> OTHER INFORMATION: internal peptide

<400> SEQUENCE: 30

Lys Lys Ala Leu Arg Arg Gln Glu Thr Val Asp Ala Leu
 1               5                  10

<210> SEQ ID NO 31
<211> LENGTH: 10
<212> TYPE: PRT
<213> ORGANISM: Artificial Sequence
<220> FEATURE:
<223> OTHER INFORMATION: Description of Artificial Sequence:synthetic
      peptide
<223> OTHER INFORMATION: internal peptide

<400> SEQUENCE: 31

Arg Arg Arg Glu Glu Glu Thr Glu Glu Glu
 1               5                  10

<210> SEQ ID NO 32
<211> LENGTH: 25
<212> TYPE: PRT
<213> ORGANISM: Artificial Sequence
<220> FEATURE:
<223> OTHER INFORMATION: Description of Artificial Sequence:synthetic
      peptide
<223> OTHER INFORMATION: internal peptide

<400> SEQUENCE: 32

Lys Arg Leu Arg Arg Ser Ala His Ala Arg Lys Glu Thr Glu Phe Leu
 1               5                  10                  15

Arg Leu Lys Arg Thr Arg Leu Gly Leu
                 20                  25

```
<210> SEQ ID NO 33
<211> LENGTH: 10
<212> TYPE: PRT
<213> ORGANISM: Artificial Sequence
<220> FEATURE:
<223> OTHER INFORMATION: Description of Artificial Sequence:synthetic
      peptide
<223> OTHER INFORMATION: where at least two of the x at positions(1-3
      and 5-6) are basic amino acids, the remainder of the x
      at positions 1-3 and 5-6 being any amino acid; x
      at positions 4, 7 9 and 10 refers to any amino acid.

<400> SEQUENCE: 33

Xaa Xaa Xaa Xaa Xaa Xaa Xaa Ser Xaa Xaa
 1               5                   10

<210> SEQ ID NO 34
<211> LENGTH: 10
<212> TYPE: PRT
<213> ORGANISM: Artificial Sequence
<220> FEATURE:
<223> OTHER INFORMATION: Where x at positions 4, 7, and 10 is any amino
      acid and x at position 9 refers to any amino acid except proline.

<400> SEQUENCE: 34

Lys Lys Arg Xaa Arg Arg Xaa Ser Xaa Xaa
 1               5                   10
```

What is claimed is:

1. A pharmaceutical composition comprising a peptide comprising at least 50% sequence identity to amino acids 1 to 84 of Ndr, or a variant thereof and a pharmaceutically acceptable carrier, wherein the variant comprises (a) from 10 to 60 continuous amino acids from the activating domain of Ndr or (b) the sequence KRLRRSAHARKETEFLRLKRTRLGL (SEQ ID NO:32) or (c) at least amino acids 72 to 84 of Ndr.

2. A method for modulating the activity of a polypeptide comprising the activating domain of an Ndr family kinase selected from the group consisting of Ndr, Wts/Lats, Dbf2, cot-1 and DMK; the method comprising influencing the binding of an EF-hand containing calcium binding protein (CBP), other than calmodulin, to the polypeptide comprising the Ndr family kinase activating domain, by administering a molecular mimic of the family of the binding site of the Ndr family kinase, said molecular mimic being a peptide comprising at least 50% sequence identity to amino acids 1 to 84 of Ndr or a variant thereof wherein the variant comprises (a) from 10 to 60 continuous amino acids from the activating domain of Ndr or (b) the sequence KRLRRSAHARKETEFLRLKRTRLGL (SEQ ID NO:32) or (c) at least amino acids 72 to 84 of Ndr, said molecular mimic competing for binding sites on the CBP and reducing effective CBP-Ndr interaction.

3. An assay for Ndr family kinase activity, comprising the steps of:

(i) incubating an Ndr family kinase with a phosphate source and a peptide selected from the group consisting of the peptide comprising the general formula KKRxRRxSnx (SEQ ID NO. 34), and the peptide comprising the general formula KKRNRRLSVA (SEQ ID NO. 1); and (ii) assessing the phosphorylation state of the peptide.

4. A method for designing a pharmaceutical agent capable of influencing the binding between an EF-hand containing calcium binding protein and an Ndr family kinase activating domain at the level of the binding site, comprising the steps of:

(a) crystallizing a peptide selected from the group consisting of the peptide comprising the general formula KKRxRRxSnx (SEQ ID NO. 34), and the peptide comprising the general formula KKRNRRLSVA (SEQ ID NO. 1); and (b) determining the structure of the Ndr peptide binding site on the peptide by using the molecular model of the peptide, optionally by computer-assisted modeling; and (c) designing a molecule which fits into the Ndr-peptide binding site so as to bind to Ndr analogously to the peptide.

5. A method for designing a pharmaceutical agent capable of influencing the binding between an EF-hand containing calcium binding protein and an Ndr family kinase activating domain at the level of the binding site, comprising the steps of:

(a) forming a complex between a peptide selected from the group consisting of the peptide comprising the general formula KKRxRRxSnx (SEQ ID NO. 34), and the peptide comprising the general formula KKRNRRLSVA (SEQ ID NO. 1); and the relevant peptide binding partner;

(b) incubating the complex with a compound to be screened and monitoring for dissociation of the peptide/binding partner complex; and (c) selecting those screened compounds which either favor or impede dissociation of the complex compared to a background count.

* * * * *